United States Patent [19]

Sohda et al.

[11] Patent Number: 5,158,943

[45] Date of Patent: * Oct. 27, 1992

[54] SULFUR-CONTAINING HETEROCYCLIC COMPOUNDS

[75] Inventors: Takashi Sohda, Takatsuki; Iwao Yamazaki, Takarazuka, both of Japan

[73] Assignee: Takeda Chemical Industries, Ltd., Osaka, Japan

[*] Notice: The portion of the term of this patent subsequent to Dec. 10, 2008 has been disclaimed.

[21] Appl. No.: 704,962

[22] Filed: May 23, 1991

Related U.S. Application Data

[63] Continuation-in-part of Ser. No. 458,094, Dec. 28, 1989, Pat. No. 5,071,841.

[30] Foreign Application Priority Data

Nov. 21, 1988 [JP] Japan .................. 63-303603
Dec. 28, 1988 [JP] Japan .................. 63-335240
May 30, 1990 [JP] Japan .................. 2-141943

[51] Int. Cl.⁵ .................. A61K 31/67; A61K 31/38; C07D 337/12; C07D 409/00
[52] U.S. Cl. .................. 514/96; 514/337; 514/371; 514/431; 546/274; 548/134; 548/136; 548/195; 548/311.4; 548/311.7; 548/447; 549/5; 549/12
[58] Field of Search .............. 549/5, 12; 514/96, 337, 514/371, 431; 546/274; 548/195

[56] References Cited

FOREIGN PATENT DOCUMENTS 0310484 9/1988 European Pat. Off. .
376197 7/1990 European Pat. Off. .
1935685 1/1969 Fed. Rep. of Germany .
1259415 3/1970 United Kingdom .

OTHER PUBLICATIONS

March, Advanced Organic Chemistry, 3rd Edition, p. 484, reaction 1-15.
R. Adams, Organic Reactions, 2, p. 114 (1962).
Shin Jikken Kagaku Koza 15 Oxidization and Reduction (II).
Chem. Pharm. Bull., 30, p. 3580 (1982).
Chem. Pharm. Bull. 30, p. 3601 (1982).
Neher et al., CA 73-28902b (1970).
Hori et al., CA 111-779407 (1989).
P. H. Bell et al., JACS, vol. 90, p. 2704 (1968).

*Primary Examiner*—Cecilia Tsang
*Attorney, Agent, or Firm*—Wegner, Cantor, Mueller & Player

[57] ABSTRACT

A sulfur-containing hetrocyclic compound of the formula (I)

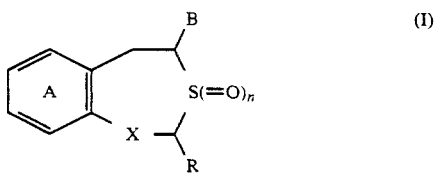

wherein the ring A is an optionally substituted benzene ring, R is a hydrogen atom or an optionally substituted hydrocarbon residue, B is a carboxyl group which may be esterified or amidated, X is —CH(OH)— or —CO—, and n is an integer of 0, 1 or 2, or its salt, which is useful in the prevention or treatment of osteoporosis.

15 Claims, No Drawings

SULFUR-CONTAINING HETEROCYCLIC COMPOUNDS

CROSS REFERENCE TO RELATED APPLICATION

The present invention is a continuation-in-part of copending application Ser. No. 07/458,094, filed Dec. 28, 1989, now U.S. Pat. No. 5,071,841 the disclosure of which is hereby incorporated herein by reference.

BACKGROUND OF THE INVENTION

1. Field of the Invention

The present invention relates to sulfur-containing heterocyclic compounds or salts thereof having activity for inhibiting bone resorption, and to a prophylactic and therapeutic agent for osteoporosis comprising the above-mentioned compound as an active ingredient.

2. Description of the Prior Art

Osteoporosis is known as a disease associated with the loss of bone calcium into the blood with the consequent decrease of bone mass which causes the bones to become fragile and liable to be fractured.

The cardinal manifestations of osteoporosis are kyphosis and fracture of thoracic vertebrae lumbar vertebrae, femoral neck, distal ends of radii, ribs, proximal ends of humeri and so on. The cause of such malady varies from endocrine disorder to nutritional disorder. The therapeutic drugs used in such cases are estrogens, calcitonin (calcium regulating hormone), vitamin D, calcium preparations and so on.

However, these therapeutic approaches are not effective enough in that symptoms and patients which can be treated are limited and, moreover, they are not definitely effective in preventing or alleviating the loss of bone mass.

SUMMARY OF THE INVENTION

As a result of earnest studies for developing more general agents directly acting on bone to inhibit bone resorption, the inventors of this invention have formed that 3-benzothiepine derivatives of the formula (I) possess excellent activity for inhibiting bone resorption.

Thus, this invention provides (1) a sulfur-containing heterocyclic compound represented by the general formula (I):

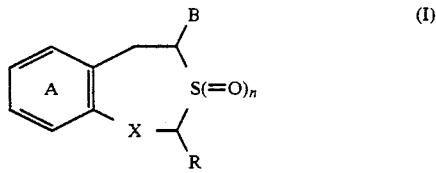

wherein the ring A is an optionally substituted benzene ring, R is a hydrogen atom or an optionally substituted hydrocarbon residue, B is a carboxyl group which may be esterified or amidated, X is —CH(OH)— or —CO—, and n is an integer of 0, 1 or 2, or its salt;

(2) a compound of the above formula (I) wherein the ring A is a benzene ring which may be substituted by one or more substituents of (a) a halogen atom, (b) an optionally substituted straight-chain or branched-chain alkyl group, (c) an optionally substituted hydroxy group, (d) an optionally substituted mercapto group and (e) an optionally substituted amino group, or its salt;

(3) a process for preparing a sulfur-containing heterocyclic compound represented by the following formula (Ia):

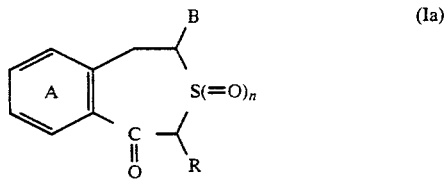

wherein the symbols have the same meanings as defined above, or its salt, which comprises subjecting a compound represented by the general formula (II):

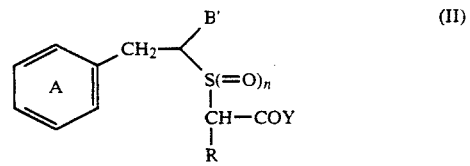

wherein B' is an esterified carboxyl group, Y is a hydroxy group or a halogen atom, and other symbols have the same meanings as defined above, or its salt to cyclization reaction; performing, if necessary, an oxidation or/and hydrolysis, hydrolysis followed by amidation, or hydrolysis followed by amidation and oxidation;

(4) a process for preparing a sulfur-containing heterocyclic compound represented by the general formula (Ib):

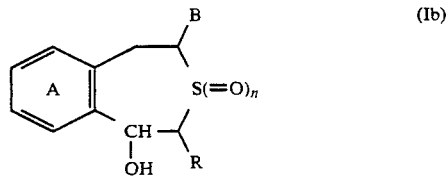

wherein the symbols have the same meanings as defined above, or its salt, which comprises subjecting the compound (Ia) or its salt to reduction; and (5) a prophylactic and therapeutic agent for osteoporosis comprising the sulfur-containing heterocyclic compound (I) or its pharmaceutically acceptable salt and a pharmaceutically acceptable carrier or diluent.

PREFERRED EMBODIMENT OF INVENTION

In the formula (I), examples of the substituents on the substituted benzene ring represented by the ring A are a halogen atom, nitro group, an optionally substituted alkyl group, an optionally substituted hydroxy group, an optionally substituted mercapto group, an amino group, an acyl group, a mono- or di-alkoxyphosphoryl group, a phosphono group, an optionally substituted aryl group, an optionally substituted aralkyl group or an optionally substituted aromatic heterocyclic group. The benzene ring may be substituted by one to four, preferably one or two of such substituents, which may be the same or different.

The halogen atom may be fluorine, chlorine, bromine or iodine.

The alkyl group in the optionally substituted alkyl group is preferably a straight-chain, branched-chain or cycloalkyl group having one to ten carbon atoms such as methyl, ethyl, propyl, isopropyl, butyl, isobutyl, sec-butyl, tert-butyl, pentyl, isopentyl, neopentyl, hexyl, heptyl, octyl, nonyl or decyl, or a cycloalkyl group having three to seven carbon atoms such as cyclopropyl, cyclobutyl, cyclohexyl or cycloheptyl. These alkyl groups may be substituted by one to three substituents such as a halogen atom (e.g., fluorine, chlorine, bromine or iodine), hydroxy group, an alkoxy group having one to six carbon atoms (e.g., methoxy, ethoxy, propoxy, butoxy or hexyloxy), a mono- or di-$C_{1-6}$ alkoxyphosphoryl group and/or phosphono group.

Examples of the substituted alkyl groups are trifluoromethyl, 2,2,2-trifluoroethyl, trichloromethyl, hydroxymethyl, 2-hydroxyethyl, 2-methoxyethyl, 2-diethoxyphosphorylethyl or phosphonomethyl.

Examples of the optionally substituted hydroxy groups are hydroxy, or hydroxy having an appropriate substituent, especially a protecting group for hydroxy, such as an alkoxy, alkenyloxy, aralkyloxy, acyloxy or aryloxy. Preferably, the alkoxy group is a straight-chain or branched-chain alkoxy group having one to ten carbon atoms such as methoxy, ethoxy, propoxy, isopropoxy, butoxy, isobutoxy, sec-butoxy, tert-butoxy, pentoxy, isopentoxy, neopentoxy, hexyloxy, heptyloxy or nonyloxy, or a cycloalkoxy group having four to six carbon atoms such as cyclobutoxy, cyclopentoxy or cyclohexyloxy. Preferably, the alkenyloxy group is an alkenyloxy group having two to ten carbon atoms such as allyloxy, crotyloxy, 2-pentenyloxy, 3-hexenyloxy, 2-cyclopentenylmethoxy, 2-cyclohexenylmethoxy or the like. Preferably, the aralkyloxy group is an aralkyloxy group having six to nineteen carbon atoms, especially a $C_{6-14}$ aryl-$C_{1-4}$ alkyloxy group (e.g., benzyloxy or phenethyloxy) Preferably, the acyloxy group is an alkanoyloxy, e.g., an alkanoyloxy group having two to ten carbon atoms (e.g., acetyloxy, propionyloxy, n-butyryloxy, isobutyryloxy or hexanoyloxy) Preferably, the aryloxy group is an aryloxy group having six to fourteen carbon atoms (e.g., phenoxy or biphenyloxy) These groups may be substituted by one to three substituent groups such as the above-mentioned halogen atom, hydroxy group, alkoxy group having one to six carbon atoms or mono- or di-alkoxyphosphoryl having one to six carbon atoms.

Examples of the substituted hydroxy groups are trifluoromethoxy, 2,2,2-trifluoroethoxy, difluoromethoxy, 2-methoxyethoxy, 4-chlorobenzyloxy or 2-(3,4-dimethoxyphenyl)ethoxy.

Examples of the optionally substituted mercapto groups are mercapto, or mercapto having an appropriate substituent, especially a protecting group for mercapto, such as an alkylthio, aralkylthio or acylthio. Preferably, the alkylthio group is a straight-chain or branched-chain alkylthio group having one to ten carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio or nonylthio), or a cycloalkylthio group having four to seven carbon atoms (e.g., cyclobutylthio, cyclohexylthio or cyclopentylthio). Preferably, the aralkylthio group is an aralkylthio group having seven atoms, especially a $C_{6-14}$ aryl-$C_{1-4}$ alkylthio group such as benzylthio or phenethylthio. Preferably, the acylthio group is an alkanoylthio, e.g., an alkanoylthio group having two to ten carbon atoms (e.g., acetylthio, propionylthio, n-butyrylthio, isobutyrylthio or hexanoylthio). These groups may be substituted by one to three substituents such as the above-mentioned halogen atom, hydroxy group, alkoxy group having one to six carbon atoms or mono- or di-alkoxyphosphoryl group having one to six carbon atoms.

Specific examples of the substituted mercapto groups are trifluoromethylthio, difluoromethylthio, 2,2,2-trifluoroethylthio, 2-methoxyethylthio, 4-chlorobenzylthio, 3,4-dichlorobenzylthio, 4-fluorobenzylthio or 2-(3,4-dimethoxyphenyl)ethylthio.

Usable acyl groups are those derived from organic carboxylic acids, or from organic sulfonic acids having one to six hydrocarbon (e.g., methyl, ethyl, n-propyl, iso-propyl, hexyl or phenyl). Examples of the organic carboxylic acyl groups are formyl, a $C_{1-10}$ alkyl-carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl or cycloheptanecarbonyl), a $C_{2-10}$ alkenyl-carbonyl group (e.g., crotonyl or 2-cyclohexenecarbonyl), a $C_{6-14}$ aryl-carbonyl group (e.g., benzoyl or the like), a $C_{7-19}$ aralkyl-carbonyl group e.g., phenylacetyl or the like), a 5- or 6-membered aromatic heterocycle-carbonyl group (e.g., nicotinoyl or 4-thiazolylcarbonyl) or a 5- or 6-membered aromatic heterocycle-acetyl group (e.g., 3-pyridylacetyl or 4-thiazolylacetyl) Examples of the sulfonic acyl groups having a hydrocarbon group of one to six carbon atoms are methanesulfonyl, ethanesulfonyl or bezenesulfonyl. The above-mentioned acyl groups may be substituted with the above-mentioned halogen atom, hydroxy group, alkoxy group having one to six carbon atoms, amino group or alkyl group having one to six carbon atoms, in the number of one to three.

Specific examples of the substituted acyl groups are trifluoroacetyl, 3-cyclohexyloxypropionyl, 4-chlorobenzoyl, 6-chloronicotinoyl or 2-methyl-4-phenyl-5-thiazolylacetyl.

Examples of the substituents in the substituted amino group are, the same or different, the above-mentioned alkyl group having one to ten carbon atoms, alkenyl group having two to ten carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl or 3-methyl-2-buten-1-yl), aryl group having six to fourteen carbon atoms (e.g., phenyl, naphthyl or anthryl) or aralkyl group having seven to nineteen carbon atoms or acyl group, in the number of one or two. These substituents may be substituted with the halogen atom, alkoxy group having one to three carbon atoms, monophosphono or di-$C_{1-6}$ alkoxyphosphoryl group or group.

Examples of the substituted amino groups are methylamino, dimethylamino, ethylamino, diethylamino, dibutylamino, diarylamino, cyclohexylamino, phenylamino, N-methyl-N-phenylamino, acetylamino, propionylamino, valerylamino, benzoylamino or methanesulfonylamino.

Specific examples of the mono- or di-alkoxyphosphoryl group are those having a lower alkoxy group such as dimethoxyphosphoryl, diethoxyphosphoryl, dipropoxyphosphoryl, diisopropoxyphosphoryl, dibutoxyphosphoryl or ethylenedioxyphosphoryl.

Examples of the aryl groups in the optionally substituted aryl group are those having six to fourteen carbon atoms such as phenyl, naphthyl or anthryl. These groups may be substituted with the alkyl group having one to six carbon atoms, halogen atom, hydroxy group or alkoxy group having one to six carbon atoms, in the number of one to three.

Specifically, the substituted aryl group is 4-chlorophenyl, 3,4-dimethoxyphenyl, 4-cyclohexylphenyl or 5,6,7,8-tetrahydro-2-naphthyl.

Examples of the aralkyl groups in the optionally substituted aralkyl group are those having seven to nineteen carbon atoms such as benzyl, naphthylethyl or trityl. The aromatic ring in these groups may be substituted with an alkyl group having one to six carbon atoms, halogen atom, hydroxy group or alkoxy group having one to six carbon atoms in the number of one to three. Specifically, the substituted aralkyl group is 4-chlorobenzyl, 3,4-dimethoxybenzyl, 2-(4-isopropylphenyl)ethyl or 2-(5,6,7,8-tetrahydro-2-naphthyl)ethyl.

Preferably, the aromatic heterocyclic group in the optionally substituted aromatic heterocyclic group is a 5- or 6-membered aromatic heterocyclic group having one to four hetero atoms of nitrogen, oxygen and/or sulfur atoms such as furyl, thienyl, imidazolyl, thiazolyl, oxazolyl or thiadiazolyl, which may be substituted with an alkyl group having one to six carbon atoms, halogen atom, hydroxy group or alkoxy group having one to six carbon atoms, in the number of one to three.

When the benzene ring is substituted with two alkyl groups at the adjacent positions, these groups may form an alkylene group represented by the formula —$(CH_2)_m$— (wherein m is an integer of 3 to 5), such as trimethylene, tetramethylene or pentamethylene. When the benzene ring is substituted with two alkoxy groups at the adjacent positions, these groups may form an alkylenedioxy group represented by the formula —O—$(CH_2)_k$—O— (wherein k is an integer of 1 to 3), such as methylenedioxy, ethylenedioxy or trimethylenedioxy. In these cases, a 5- to 7- membered ring is formed together with the carbon atoms on the benzene ring.

Examples of the hydrocarbon groups in the optionally substituted hydrocarbon group represented by R are the above-mentioned alkyl group (preferably having one to ten carbon atoms), alkenyl group (preferably having two to ten carbon atoms), aryl group (preferably having six to fourteen carbon atoms) or aralkyl group (preferably having seven to nineteen carbon atoms). Examples of the substituents on the hydrocarbon groups are the above-mentioned 5- or 6-membered aromatic heterocyclic group, halogen atom, dialkoxyphosphoryl group or phosphono group.

Preferably, R is an unsubstituted alkyl group having one to six carbon atoms, such as methyl, ethyl, propyl, isopropyl, butyl, isobutyl, sec-butyl, tert-butyl, pentyl, neopentyl or hexyl.

Examples of the esterified carboxyl groups represented by B are an alkoxycarbonyl group preferably having one to ten carbon atoms (e.g., methoxycarbonyl, ethoxycarbonyl, propoxycarbonyl or butoxycarbonyl), an aryloxy group preferably having six to fourteen carbon atoms (e.g., phenoxycarbonyl) or an aralkyloxycarbonyl group preferably having seven to nineteen carbon atoms (e.g., benzyloxycarbonyl).

The amidated carboxyl group represented by B is preferably an optionally substituted carbamoyl group represented by the formula —$CON(R^1)(R^2)$ wherein $R^1$ and $R^2$ each is a hydrogen atom, an optionally substituted hydrocarbon group or an optionally substituted 5- to 7-membered heterocyclic group.

Examples of the hydrocarbon groups in the optionally substituted hydrocarbon group represented by $R^1$ or $R^2$ are an alkyl group, preferably the above-mentioned alkyl group having one to ten carbon atoms, an alkenyl group, preferably an alkenyl group having two to ten carbon atoms, an aryl group, preferably an aryl group having six to fourteen carbon atoms or an aralkyl group, preferably an aralkyl group having seven to nineteen carbon atoms. These groups may be substituted, in the number of one to three, with a halogen atom (e.g., fluorine, chlorine, bromine or iodine), a hydroxy group, an alkoxy group having one to six carbon atoms, an amino group which may be substituted with an alkyl group having one to six carbon atoms (e.g., dimethylamino, diethylamino or dipropylamino), an amino group which may be substituted with an acyl group such as an alkanoyl group having one to ten carbon atoms (e.g.,acetylamino, propionylamino or benzoylamino), a carbamoyl group which may be substituted with an alkyl group having one to six carbon atoms (e.g., dimethylcarbamoyl or ethoxycarbamoyl), an alkoxycarbonyl group having one to six carbon atoms (e.g., methoxycarbonyl or ethoxycarbonyl), a mono- or di-alkoxyphosphoryl group (e.g., dimethoxyphosphoryl, diethoxyphosphoryl or ethylenedioxyphosphoryl), a phosphono group or the above-mentioned aromatic heterocyclic group.

Examples of the 5- to 7-membered heterocyclic groups in the optionally substituted 5- to 7-membered heterocyclic group represented by $R^1$ or $R^2$ are a 5- to 7-membered heterocyclic group containing one sulfur, nitrogen or oxygen atom, a 5- or 6-membered heterocyclic group containing two to four nitrogen atoms or a 5- or 6-membered heterocyclic group containing one to two nitrogen atoms and one sulfur or oxygen atom. These heterocyclic groups may condense with a 6-membered ring containing two or less nitrogen atoms, a benzene ring or a 5-membered ring containing one sulfur atom.

Substituents on the optionally substituted 5- to 7-membered heterocyclic group represented by $R^1$ or $R^2$ may be the above-mentioned substituents on the optionally substituted hydrocarbon group represented by $R^1$ or $R^2$.

Examples of the above heterocyclic groups are 2-pyridyl, 3-pyridyl, 4-pyridyl, pyrimidinyl, pyrazinyl, pyridazinyl, pyrazolyl, imidazolyl, thiazolyl, oxazolyl, isoxazolyl, pyrido[2,3-d]-pyrimidyl, benzopyranyl, 1,8-naphthyridinyl, 1,5-naphthyridinyl, 1,6-naphthyridinyl, 1,7-naphthyridinyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl, morpholino or the like.

$R^1$ and $R^2$ may combinedly form a 5- to 7-membered ring together with a carbon chain which may contain an oxygen, sulfur or nitrogen atom. Thus formed ring represents a 5- to 7-membered ring formed together with the nitrogen atom of the acid amide in the formula (I). Examples of the ring are morpholine, piperidine, thiomorpholine, homopiperidine, pyrrolidine, thiazolidine, azepine or the like.

Specifically, the substituted alkyl group represented by $R^1$ or $R^2$ may be trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N- ethylamino)ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tert-butoxycarbonylpropyl, 2-diethoxyphosphorylethyl, 3-dipropoxyphosphorylpropyl, 4-dibutoxyphosphorylbutyl, ethylenedioxyphosphorylmethyl, 2-phosphonoethyl, 3-phosphonopropyl or the like.

Specifically, the substituted aralkyl groups may be 4-chlorobenzyl, 3-(2-fluorophenyl)propyl, 3-methoxybenzyl, 3,4-dimethoxyphenethyl, 4-ethylbenzyl, 4-(3-trifluoromethylphenyl)butyl, 4-acetylaminobenzyl, 4-dimethylaminophenethyl, 4-diethoxyphosphorylbenzyl, 2-(4-dipropoxyphosphorylmethylphenyl)ethyl or the like.

Specifically, the substituted aryl groups may be 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-diethoxyphosphorylmethylphenyl, 4-dipropoxyphosphorylphenyl, 4-(2-phosphonoethyl)phenyl, 4-phosphonomethylphenyl, 4-phosphonophenyl or the like.

Specifically, the substituted 5- to 7-membered heterocyclic group may be 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazole-5-yl, 5-methyl-1,3,4-thiadiazole-2-yl, 5-acetylamino-2-pyrimidyl, 3-methyl-2-thienyl, 4,5-dimethyl-2-furanyl, 4-methyl-2-morpholinyl or the like.

Examples of the esterified carboxyl groups represented by B' are those defined in B. Preferably, the esterified carboxyl group represented by B' is an ester with an alkyl group having one to six carbon atoms, for example, methyl, ethyl, propyl, isopropyl, butyl, tert-butyl, pentyl, neopentyl or hexyl ester or an aralkylester, especially an ester with an aralkyl group having seven to nineteen carbon atoms, for example, benzyl, phenethyl or 3-phenylpropyl ester.

In the above, preferably the ring A is a benzene ring which may be substituted by the same or different, one or more (preferably one or two) substituents of (a) a halogen atom, (b) an optionally substituted straight or branched chain alkyl group having 1 to 10 carbon atoms, (c) an optionally substituted hydroxy group, (d) an optionally substituted mercapto group and/or (e) an optionally substituted amino group.

Examples of substituents on each substituted group in (b), (c), (d) and (e) are the above-mentioned respective substituents on each group.

More preferably, the ring A is a benzene ring which may be substituted by the same or different, one or two substituents of a halogen atom, a straight or branched chain alkyl group having 1 to 10, preferably 1 to 5 carbon atoms, a straight or branched chain alkoxy group having 1 to 10, preferably 1 to 5 carbon atoms, an alkylenedioxy group represented by the formula of $-O-(CH_2)_k-)-$ wherein k is an integer of 1 to 3 and/or a straight or branched chain alakylthio group having 1 to 10, preferably 1 to 5 carbon atoms.

The substituent B is preferably a carboxyl group, a $C_{1-10}$ alkoxy-carbonyl group or a group represented by the formula $-CON(R^1)(R^2)$ wherein $R^1$ and $R^2$ each is a hydrogen atom, an optionally substituted hydrocarbon group or an optionally substituted 5- to 7-membered heterocyclic group.

With respect to the above $R^1$ and $R^2$, preferably $R^1$ is a hydrogen atom or a $C_{1-10}$ alkyl group, and $R^2$ is a phenyl or phenyl-$C_{1-3}$ alkyl group which may be substituted by a halogen atom, $C_{1-6}$ alkoxy, mono- or di-alkoxyphosphoryl, mono- or di-alkoxyphosphoryl-$C_{1-3}$ alkyl or $C_{1-6}$ alkoxycarbonyl, or a 5- or 6-membered heterocyclic group having one or two nitrogen atoms or one nitrogen atom and one sulfur atom which may be substituted by a phenyl group.

The substituent R is preferably a hydrogen atom, an alkyl group having one to six carbon atoms or a phenyl group.

The compound (I) or its salt can be prepared by any known methods, for example, by the following methods. The salts of the compounds described below are similar to or the same as those of the compounds (I).

(1) Method A

A compound represented by the following formula (Ia'):

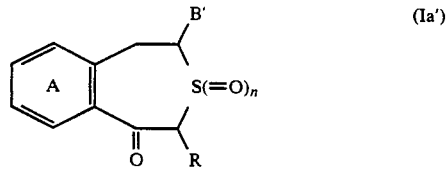

wherein the symbols have the same meanings as defined above, or its salt can be prepared by subjecting the compound (II) or its salt to a cyclization reaction.

The cyclization reaction can be carried out by the same manner as the conventional Friedel-Crafts Reaction. Thus, it can utilize any known method, for example, as described in R. Adams, Organic Reactions, 2, pp.114 [John Wiley & Sons, Inc. New York, (1962)]; Shin Jikken Kagaku Koza 14, Synthesis and Reaction of Organic Compound (II) [Maruzen, (1977)].

The reaction is usually carried out in a solvent which does not impede the reaction or in the absense of a solvent. Usable solvents are aromatic hydrocarbons such as benzene, toluene or xylene, halogenated hydrocarbons such as chloroform, dichloromethane, 1,2-dichloroethane or 1,1,2,2-tetrachloroethane, ethers such as diethyl ether or tetrahydrofuran, nitrobenzene, nitromethane, carbon disulfide or the like. The above solvents may be used singly or as a mixture thereof. The reaction is conducted in the presence of a Lewis acid such as hydrogen fluoride, sulfuric acid, phosphoric acid, phosphoric anhydride, aluminum chloride, tin tetrachloride, zinc chloride or the like. The amount of the Lewis acid to be used is about 2 to 10 mols per mol of the compound (II) or its salt. The reaction temperature is in the range of about $-20°$ C. to $200°$ C., preferably about $0°$ C. to $100°$ C. The reaction time is usually about 30 minutes to 100 hours, preferably about 1 hour to 30 hours.

(2) Method B

A compound represented by the following formula (Ia"):

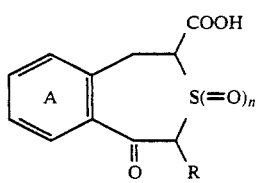

wherein the symbols have the same meanings as defined above, or its salt can be prepared by subjecting the compound (Ia') or its salt to a hydrolysis reaction.

The hydrolysis can be carried out in water or in an aqueous solvent according to the conventional methods.

Usable aqueous solvents include a mixture of water and an alcohol (such as methanol or ethanol), an ether (such as tetrahydrofuran or dioxane), N,N-dimethylformamide, dimethylsulfoxide or acetone.

The reaction is carried out in the presence of a base such as potassium carbonate, sodium carbonate, sodium hydroxide, potassium hydroxide or lithium hydroxide, or an acid such as hydrochloric acid, sulfuric acid, acetic acid or hydrobromic acid. Preferably, the acid or the base is used in an excess amount (base: 1.2 to 6 equivalents; acid: 2 to 50 equivalents) to the compound (Ia'.) The reaction is usually conducted at about −20° C. to 150° C., preferably about −10° C. to 100° C.

(3) Method C

A compound represented by the following formula (Ic):

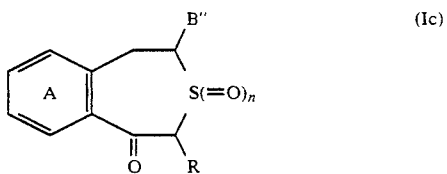

wherein B" is an amidated carboxyl group and symbols have the same meanings as defined above, or its salt can be prepared by subjecting the compound (Ia") or its salt to amidation reaction.

It can be carried out by reacting the compound (Ia") or its salt with an amine compound.

The amine compound is preferably a compound of the following formula (III):

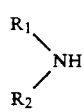

wherein the symbols have the same meanings as defined above. The reaction of the compound (Ia") or its salt with the amine compound can be conducted by the same manner as in the condensation reaction well-known in the field of peptide synthesis.

The reaction can be carried out according to any known methods, e.g., azide method, chloride method, acid anhydride method, mixed anhydride method, DCC method, activated ester method, method using Woodward's reagent K, carbonyldiimidazole method, redox reaction method, DCC/HONB method and method using diethyl phosphorocyanidate, those of which are disclosed in any one of documents, such as M. Bodansky and M. A. Ondetti, Peptide Synthesis, [Interscience, New York, (1966)]; F. M. Finn and K. Hofmann, The Proteins, 2, edited by H. Nenrath, R. L. Hill, [Academic Press Inc., New York, (1976)]; Nobuo Izumiya, Foundation and Experiment of Peptide Synthesis, [Maruzen, (1985)].

For example, the reaction can be carried out by the following method. The amine compound (III) as the starting material may be used in an amount of about 1 to 10 mols per mol of the compound (Ia ) or its salt.

The reaction is conducted in a solvent which does not impede the reaction.

Examples of such solvents are N,N-dimethylformamide, dimethylsulfoxide, pyridine, chloroform, dichloromethane, ethyl acetate, ethyl ether, tetrahydrofuran, acetonitrile or mixtures thereof. The above-mentioned solvents may be used in anhydrous or hydrous condition.

The reaction temperature is usually about −20° C. to 50° C., preferably about −10° C. to 30° C. The reaction time is about 1 to 100 hours, preferably about 2 to 40 hours.

(4) Method D

A compound represented by the following formula (Id):

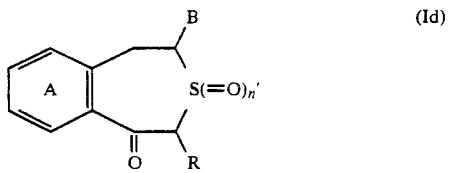

wherein n' is an integer of 1 or 2 and the other symbols have the same meanings as defined above, or its salt can be prepared by subjecting the compounds (Ia'), (Ia") or (Ic) (wherein n is 0 respectively) or its salt to oxidation reaction.

The reaction can be carried out by oxidizing the above compound or its salt with an oxidizing agent in accordance with the conventional method. The oxidizing agent is preferably a mild agent which does not substantially act on the skeleton of the sulfur-containing heterocyclic compound, such as m-chloroperbenzoic acid, hydrogen peroxide, peresters, sodium metaperiodate or the like.

The reaction is carried out in an organic solvent which does not impede the reaction.

Examples of the solvents are halogenated hydrocarbons (e.g., dichloromethane, chloroform or dichloroethane), hydrocarbons (e.g., benzene or toluene), alcohols (e.g., methanol, ethanol or propanol) or mixtures thereof.

In the case where the oxidizing agent is used in an amount equivalent to or less than the amount of the compound (Ia'), (Ia") or (Ic) (wherein n is 0 respectively) or its salt, the compound of the formula (Id) in which n' is 1 is predominantly formed. The compound of the formula (Id) in which n' is 2 is prepared by oxidizing the compound of the formula (Id) in which n' is 1 in the case where the oxidizing agent is used in an amount more than that of each of these compounds or its salt.

The reaction proceeds at or below room temperature (10° C. to 30° C.), preferably about −50° C. to 20° C.

The reaction time is about 30 minutes to 10 hours.

(5) Method E

The compound (Ib) or its salt can be prepared by subjecting the compound (Ia′), (Ia″), (Ic) or (Id) or its salt to reduction.

The compound of the formula (I) in which X is —CH(OH)—, i.e., the compound (Ib), or its salt can be prepared with this reaction by using the compounds prepared in Methods A to D.

This reaction can be conducted by any known reduction, e.g., the method disclosed in Shin Jikken Kagaku Koza 15, Oxidization and Reduction (II) [Maruzen, (1977)].

This reaction can be carried out by treating the compound (Ia′), (Ia″), (Ic) or (Id) or its salt with a reducing agent. Usable reducing agents are a metal hydride complex such as alkali metal borohydrides (e.g., sodium borohydride or lithium borohydride), organic tin compounds (e.g., triphenyltin hydride), nickel compounds, zinc compounds or catalytic reduction systems comprising transition metal catalyst such as palladium, platinum. rhodium or the like in the combination with hydrogen. Further, hydrogen transfer reduction is usable.

This reaction is carried out in an organic solvent which does not impede the reaction.

Examples of the solvents are halogenated hydrocarbons e.g., dichloromethane, chloroform or dichloroethane), hydrocarbons (e.g., benzene or toluene), alcohols (e.g., methanol, ethanol, propanol or isopropanol), ethers (e.g., diethylether, dioxane or tetrahydrofuran), amides (e.g., N,N-dimethylformamide) or mixtures thereof, which are suitably selected in accordance with the kind of the reducing agent used.

The reaction temperature is about 0° C. to 130° C., preferably about 10° C. to 100° C.

The reaction time is about 30 minutes to 24 hours.

(6) Method F

This is a method for producing a phosphono group-containing compound or its salt from a mono- or di-alkoxyphosphoryl group-containing compound which is selected among the compounds prepared in Methods A to F.

This reaction can be carried out in an organic solvent which does not impede the reaction by using an inorganic acid such as hydrochloric acid, hydrobromic acid or the like or a trialkylsilyl halide.

When the inorganic acid such as hydrochloric acid or hydrobromic acid is used, the solvent may be an alcohol such as methanol, ethanol, 2-methoxyethanol, ethylene glycol, propanol, butanol or the like, water, or mixtures thereof. The acid is usually used in an excess amount. The reaction temperature is about 0° C. to 150° C., preferably about 30° C. to 100° C. The reaction time is about 1 to 50 hours.

When a trialkylsilyl halide such as chlorotrimethylsilane, bromotrimethylsilane or iodotrimethylsilane is used, the solvent may be a halogenated hydrocarbon such as carbon tetrachloride, chloroform, dichloromethane, 1,2-dichloroethane or 1,1,2,2-tetrachloroethane, or acetonitrile or mixtures thereof.

The alkylsilyl halide is used in an amount of about 1 to 10 equivalents, preferably about 2 to 5 equivalents, to the mono- or di-alkoxyphosphoryl group-containing compound. The reaction temperature is about −30° C. to 100° C., preferably about −10° C. to 50° C. The reaction time is about 30 minutes to 100 hours.

The sulfur-containing heterocyclic compound (I) or its salt thus obtained can be isolated and purified, e.g., by a conventional method such as filtration, concentration, concentration under reduced pressure, solvent extraction, crystallization, recrystallization, redistribution or chromatography. The same separation and purification procedures are also applicable to the preparation of the starting compound described below.

The starting compound (II) of the present invention can be prepared by known methods, e.g., by the following method.

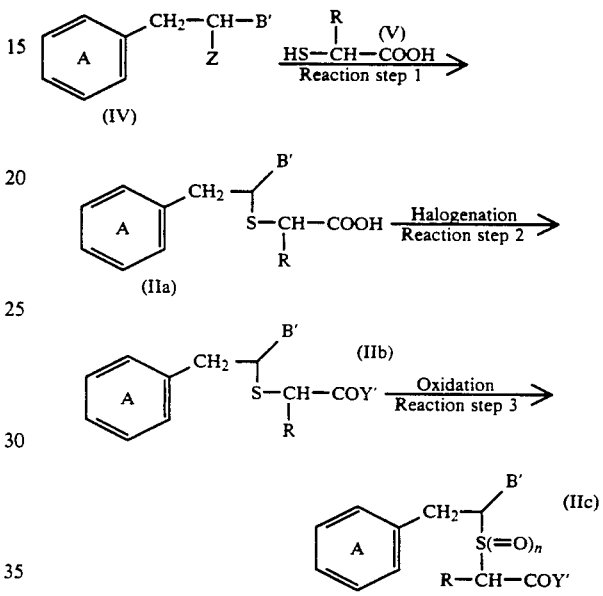

In the above formula, Z is a leaving group, Y′ is a halogen atom and the other symbols have the same meanings as defined above.

Reaction Step 1

In this step, the compound (IIa) or its salt is prepared by reacting a compound (IV) or its salt with a compound (V) or its salt in the presence of a base.

Examples of the leaving groups represented by Z are a halogen, preferably chlorine, bromine or iodine, or an activated hydroxy group by esterification, for example, a residue of organic sulfonic acid (e.g., p-toluenesulfonyloxy group, a $C_{1-4}$ alkylsulfonyloxy group such as methanesulfonyloxy group) or a residue of organic phosphoric acid (e.g., diphenylphosphoryloxy group, dibenzylphosphoryloxy group or dimethylphosphoryloxy group).

The reaction of the compound (IV) or its salt with the compound (V) or its salt is conducted in a solvent which does not impede the reaction.

Examples of the solvents are aromatic hydrocarbons such as benzene, toluene or xylene, ethers such as dioxane, tetrahydrofuran or dimethoxyethane, alcohols such as methanol, ethanol or propanol, esters such as ethyl acetate, nitriles such as acetonitrile, pyridines such as pyridine or lutidine, amides such as N,N-dimethylformamide, sulfoxides such as dimethylsulfoxide, halogenated hydrocarbons such as chloroform, dichloromethane, 1,2-dichloroethane or 1,1,2,2-tetrachloroethane, ketones such as acetone or 2-butanone or mixtures thereof.

This reaction is carried out in the presence of an inorganic base (e.g., sodium hydride, potassium hydride, potassium carbonate or sodium hydrogen carbonate), or an organic base such as tertiary amine (e.g., pyridine, triethylamine or N,N-dimethylaniline).

The base is used in an amount of about 1 to 5 mols to the compound (IV) or its salt.

This reaction is usually conducted at about −20° C. to 150° C., preferably about −10° C. to 100° C.

The starting compound (IV) or its salt can be synthesized according to the method disclosed in Chem. Pharm. Bull., 30, p. 3580 (1982); or Chem. Pharm. Bull., 30, p. 3601 (1982).

Reaction Step 2

In this step, the compound (IIb) or its salt can be prepared by subjecting the compound (IIa) or its salt to halogenation.

This reaction is conducted according to known methods, e.g., the method disclosed in Shin Jikken Kagaku Koza 14, Synthesis and Reaction of Organic Compound [II], [Maruzen, (1977)].

The reaction can be conducted by reacting the compound (IIa) or its salt with a halogenating agent such as a chlorinating agent (e.g., phosphorus pentachloride, thionyl chloride or oxalyl chloride).

The reaction is carried out in a solvent which does not impede the reaction or without a solvent.

Examples of the solvents are aromatic hydrocarbons such as benzene, toluene or xylene, ethers such as dioxane, tetrahydrofuran or dimethoxyethane, nitriles such as acetonitrile, amides such as N,N-dimethylformamide, halogenated hydrocarbons such as chloroform, dichloromethane, 1,2-dichloroethane or 1,1,2,2-tetrachloroethane or mixtures thereof.

The reaction is carried out under heating (about 20° C. to 120° C.). The reaction time is about 1 hour to 20 hours.

Reaction Step 3

The compound (IIc) or its salt can be prepared by subjecting the compound (IIb) or its salt to oxidation.

The oxidation can be performed by the same manner as in Method D.

The compound (IIa) can also be prepared by the following method.

(IV)

(VII)

(VIII)

-continued (IIa)

In the formula, R' is a lower alkyl group and the other symbols have the same meanings as defined above.

Reaction Step 1

In this step, a compound (VII) or its salt is prepared by reacting the compound (IV) or its salt with the compound (VI) or its salt in the presence of a base.

Examples of the leaving groups represented by Z are those defined above, and examples of the lower alkyl groups are those having one to four carbon atoms such as methyl, ethyl, propyl, isopropyl, butyl or isobutyl.

The reaction of the compound (IV) or its salt with the compound (VI) or its salt is conducted in a solvent which does not impede the reaction.

Examples of the solvents are aromatic hydrocarbons such as benzene, toluene or xylene, ethers such as dioxane, tetrahydrofuran or dimethoxyethane, esters such as ethyl acetate, amides such as N,N-dimethylformamide, sulfoxides such as dimethylsulfoxide, halogenated hydrocarbons such as chloroform, dichloromethane, 1,2-dichloroethane or 1,1,2,2-tetrachloroethane, ketones such as acetone or 2-butanone or mixtures thereof.

This reaction is carried out in the presence of an inorganic base (e.g., such as sodium hydride, potassium hydride, potassium carbonate or sodium hydrogen carbonate), or an organic base such as tertiary amine (e.g., pyridine, triethylamine or N,N-dimethylaniline).

The base is used in an amount of about 1 to 5 mols to the compound (IV) or its salt.

This reaction is usually conducted at about −20° C. to 150° C., preferably about −10° C. to 100° C.

The reaction time is usually about 30 minutes to 10 hours.

Reaction Step 2

In this step, a compound (VIII) or its salt can be prepared by subjecting the compound (VII) or its salt to hydrolysis in the presence of a base.

The reaction is carried out in a solvent which does not impede the reaction or without a solvent.

Examples of the solvents are alcohols such as methanol, ethanol, propanol, isopropanol or 2-methoxyethanol or a mixture of water and these alcohols or tetrahydrofuran, acetone, N,N-dimethylformamide or dimethyl sulfoxide.

The reaction is carried out in the presence of an inorganic base such as sodium hydroxide, potassium hydroxide or potassium carbonate, or an organic base such as ammonia or secondary amine (e.g., dimethylamine, diethylamine, morpholine or piperidine).

The base is used in an amount of about 1 to 10 mols to the compound (VII).

The reaction is carried out at about −20° C. to 150° C., preferably about −10° C. to 80° C.

Reaction Step 3

The compound (IIa) or its salt can be prepared by reacting the compound (VIII) or its salt with a compound (IX) or its salt.

This reaction can be performed by the same manner as the reaction of (IV) or its salt with the compound (V) or its salt.

As the salt of compound (I), a pharmaceutically acceptable salt is preferably used. Examples of the pharmaceutically acceptable salts are the salt with an inorganic base such as an alkali metal (e.g., sodium or potassium) or alkaline earth metal (e.g., calcium or magnesium); salt with an organic base such as trimethylamine, triethylamine, pyridine, picoline, N,N-dibenzylethylenediamine or diethanolamine; salt with an inorganic acid such as hydrochloric acid, hydrobromic acid, hydroiodic acid, phosphoric acid, nitric acid or sulfuric acid; salt with an organic acid such as formic acid, acetic acid, trifluoroacetic acid, oxalic acid, tartaric acid, fumaric acid, maleic acid, methanesulfonic acid, bezenesulfonic acid, p-toluenesulfonic acid or citric acid; or salt with a basic or acidic amino acid such as arginine, lysine, glutamic acid.

Among the various types of salts mentioned above, said salts with bases mean salts which are formed when the compound (I) contains a carboxyl group for B and/or an acidic group such as carboxyl or sulfo on ring A or in the substituents group B or R, and said salts with acids means any and all salts formed when the compound (I) contains a basic group such as amino on ring A or in the substituent B or R.

The toxicity of the compounds (I) or their salts is very low. The compounds (I) or their salts possesses excellent activity for inhibiting bone resorption, i.e., activity for inhibiting the dissolution and diminution of bone in the body. Further, the compounds (I) or their salts of the present invention have activity for promoting bone formation.

Therefore, the compounds (I) or their salts of the present invention can be used as a drug for human beings and livestock. In other words, the compounds (I) or their salts can safely be used in the prevention and treatment of various diseases caused by bone resorption, for example, osteoporosis.

The compounds (I) or their salts of the present invention can be administered orally or parenterally (e.g., by intravenous or intramuscular injection).

Compositions for oral administration may be solid or liquid forms, specifically tablets (including sugar coated tablets and film coated tablets), pills, granules, powders, capsules (including soft capsules), syrups, elixirs, emulsions and suspensions.

Such compositions will contain conventional carriers or excipients and can be prepared by known methods. Examples of carriers or excipients are binders such as syrup, gum arabic, gelatin, sorbitol, tragacanth gum or polyvinylpyrrolidone; fillers such as lactose, sugars, corn starch, potassium phosphate or glycine; lubricants such as magnesium stearate, talc, polyethylene glycol or silica; disintegrators such as potato starch; or wetting agents such as sodium lauryl sulfate.

Compositions for parenteral administration are, e.g., injections and suppositories, the former of which includes subcutaneous, intracutaneous, intramuscular or like injections. Such injections can be prepared by suspending or emulsifying the compound (I) or its salt in or with sterile aqueous or oily liquids which are usually employed in injections, in accordance with the methods known in the art. Examples of the aqueous liquids for injections are physiological saline and isotonic solution, which may be used together with a suitable suspending agent such as sodium carboxy methylcellulose or a nonionic surfactant upon circumstances. Examples of the oily liquids are sesame oil and soybean oil, which may be used together with a solubilizing agent such as benzyl benzoate or benzyl alcohol. The injections thus prepared are usually put into ampoules.

Other active ingredients (e.g., Osten ®) having activity for inhibiting bone resorption may be mixed with these compositions to prepare compositions showing much stronger activity for inhibiting bone resorption.

The compound (I) or its salt can be used as a prophylactic and therapeutic agent for bone diseases such as osteoporosis. The daily dosage of the compound (I) or its salt varies depending upon the condition and weight of the patients or method of administration. The oral dosage is 10 to 1000 mg/day/adult (weight:50 kg), preferably 15 to 600 mg/day/adult (weight:50 kg). This dosage is administered one to three times per day.

The compounds (I) or salts thereof possess potent activity for inhibiting bone resorption, improving bone metabolism and promoting bone formation. Therefore, the compounds (I) or salts thereof can be used as a prophylactic and therapeutic agent for various diseases caused by bone resorption including osteoporosis.

The compounds (I) or salt thereof are only sparingly toxic and can be safely used.

The invention will be explained in further detail with reference to Test Examples, Reference Examples and Examples, by which this invention shall not be limited.

TEST EXAMPLE 1

Study on bone resorption inhibition

Bone resorption inhibitory activity was determined according to the method of Raisz [Journal of Clinical Investigation (J. Clin. Invest.) 44, 103–116 (1965)].

That is, a Sprague-Dawley rat at day 19 of pregnancy was subcutaneously dosed with 50 $\mu$Ci of $^{45}$Ca (a radioisotope of calcium, in $CaCl_2$). On the next day, the animal was laparotomized and the fetuses were removed aseptically. The right and left humeri (radii and ulnae) of each rat fetus were dissected from the body under the dissection microscope. The connective tissue and cartilages were removed as far as possible to prepare bone culture specimens. Each piece of bone was incubated in 0.6 ml of $BGJ_b$ medium (Fitton-Jackson modification [the tradename owned by GIBCO Laboratories, U.S.A.]) containing 2 mg/ml of bovine serum albumin at 37° C. for 24 hours. Then, incubation was carried out for additional two days in the above-mentioned medium. The radioactivities of $^{45}$Ca in the culture medium and bone were determined and the ratio (%) of $^{45}$Ca released from the bone to the medium was calculated according to the following formula.

$$A = \frac{B}{B + C} \times 100$$

A = ratio (%) of $^{45}$Ca released from the bone to the medium
B = $^{45}$Ca count in the medium
C = $^{45}$Ca count in the bone The bones from the fetuses of the same litter were similarly incubated without addition of the test compound for two days and served as controls.

The values for 5 bones per group were expressed in mean. The ratio (%) of this value for the treatment group to the control value was determined. The results are shown in Table 1.

TABLE 1

| Compounds Example No. | $^{45}$Ca release (% to control) |
|---|---|
| 25 | 69 |
| 26 | 68 |
| 28 | 61 |
| 32 | 63 |
| 37 | 63 |

TEST EXAMPLE 2

Study on therapeutic effect for osteoporosis

Oophorectomy was performed on SAM R/1 mice (13 week old). From the next day of the extirpation, a specimen of the compound obtained in Examples 24 and 30 was orally given to the mouse for 3 weeks (6 days per a week). On the next day of the final administration, the left femur of the mouse was extirpated and cut at right angle to a longitudinal axis to give ⅓ of the femur from the distal end. The piece of the femur was dipped in 0.2N aqueous potassium hydroxide solution to remove the marrows. Thereafter, the piece was transferred into a glass test tube to be dried in an electric drier for 3 hours at 100° C. and then weighed.

Tables 2 and 3 show the average value±standard error obtained from the measurement value of 6 to 8 mice in each group.

TABLE 2

| Group | Dosage (mg/kg) | Dry weight (mg) |
|---|---|---|
| Sham operation Control | 0 | 10.31** ± 0.20 |
| Oophorectomy Control | 0 | 9.42 ± 0.15 |
| Compound No. 24 Treatment Group | 100 | 10.29* ± 0.46 | significant difference relative to the average oophorectomy controls.
*p < 0.05. **p < 0.01

TABLE 3

| Group | Dosage (mg/kg) | Dry weight (mg) |
|---|---|---|
| Sham operation Control | 0 | 10.18** ± 0.18 |
| Oophorectomy Control | 0 | 9.16 ± 0.09 |
| Compound No. 30 Treatment Group | 100 | 9.88* ± 0.21 | significant difference relative to the average oophorectomy controls.
*p < 0.05, **p < 0.01

REFERENCE EXAMPLE 1

A solution of sodium nitrite (27.7 g) in water (40.0 ml) was added dropwise to a mixture of 3,4-methylenedioxyaniline (50 g), aq. HBr (47%, 125 ml) and acetone (500 ml) at 0°–5° C., followed by stirring for 20 minutes at 5° C. To the solution was added methyl acrylate (197 ml). The resultant solution was warmed to 32° C. to which cuprous oxide ($Cu_2O$) (0.5 g) was added in small portions with vigorous stirring. The mixture generates nitrogen gas due to exothermic reaction. After completing the generation of nitrogen gas, the reaction mixture was further stirred for an hour and concentrated under reduced pressure. Water was poured into the reaction mixture and the mixture was extracted with ether. The ethereal layer was washed with $H_2O$, dried ($MgSO_4$) and distilled off under reduced pressure to give methyl 2-bromo-3-(3,4methylenedioxyphenyl)propionate (56.2 g, 54%).

Bp: 148°–150 ° C./1 mmHg.

NMR(δ ppm in $CDCl_3$): 3.15(1H, q, J=14 and 7 Hz), 3,38(1H, q, J=14 and 7 Hz), 3.74(3H, s), 4.34(1H, t, J=7 Hz), 5.92(2H, s), 6.6–6.8(3H, m).

REFERENCE EXAMPLES 2–5

Compounds listed in Table 4 were obtained by the same manner as in Reference Example 1.

REFERENCE EXAMPLE 6

A solution of methyl 2-bromo-3-(3,4-methylenedioxyphenyl) propionate (28.7 g) in N,N-dimethylformamide (DMF) (30 ml) was added dropwise to a mixture of thioglycolic acid (10.1 g), triethylamine (22.3 g) and DMF (120 ml) under ice-cooling. The reaction mixture was further stirred for an hour with ice-cooling, poured into water (300 ml) and extracted with ether. The aqueous layer was acidified with cocn. HCl and extracted with ether. The ether layer was washed with water, dried ($MgSO_4$) and concentrated to give methyl 2-carboxymethylthio-3-(3,4-methylenedioxyphenyl)propionate (29.1 g, 98%) as oil.

NMR(δ ppm in $CDCl_3$): 2.92(1H, q, J=14 and 7 Hz), 3,13(1H, q, J=14 and 7 Hz), 3.35(1H, d, J=16 Hz), 3.50(1H, d, J=16 Hz), 3.6–3.8(1H, m), 3.70(3H, s), 5.93(2H, s), 6.6–6.8(3H, m).

REFERENCE EXAMPLES 7–15

Compounds listed in Table 5 were obtained by the same manner as in Reference Example 6.

REFERENCE EXAMPLE 16

A mixture of methyl 2-bromo-3-(4-methylphenyl)-propionate (25.7 g), potassium thioacetate ($CH_3COSK$) (13.7 g) and DMF (120 ml) was stirred for an hour at room temperature. The mixture was poured into water and extracted with ether. The ethereal layer was washed with water, dried ($MgSO_4$) and concentrated to give methyl 2-acetylthio-3-(4-methylphenyl)propionate (25.2 g, 100%) as an oil.

NMR(δppm in $CDCl_3$) 2.31(3H, s), 2.32(3H, s), 2,98(1H, q, J=14 and 7 Hz), 3.21(1H, q, J=14 and 7 Hz), 3.67(3H, s), 4.42(1H, t, J=7 Hz), 7.09(4H, s).

REFERENCE EXAMPLE 17

Morpholine (34.8 g) was added dropwise to a solution of methyl 2-acetylthio-3-(4-methylphenyl) propionate (25.1 g) in methanol (200 ml) at room temperature. The mixture was stirred at ambient temperature for two hours, poured into water and extracted with ether. The ethereal layer was washed with water, dried ($MgSO_4$) and concentrated. The residual oil was subjected to a silica gel column chlomatography, eluting with ethyl acetate-hexane (1:20, V/V) to give methyl 2-mercapto-3-(4-methylphenyl)propionate (18.0 g, 86%) as an oil.

NMR(δ ppm in $CDCl_3$): 2.10(1 H, d, J=9 Hz), 2.32(3H, s), 2.97(1 H, q, J=14 and 7 Hz), 3,22(1 H, q, J=14 and 7 Hz), 3.58(1 H, q, J=7 Hz), 3.69(3H, s), 7.10(4H, s).

REFERENCE EXAMPLE 18

A solution of methyl 2-mercapto-3-(4-methylphenyl)-propionate (17.5 g) in DMF (30 ml) was added dropwise to a mixture of α-bromophenylacetic acid (17.0 g), potassium carbonate (34.4 g) and DMF (120 ml), followed by stirring for an hour at room temperature. The reaction mixture was poured into water (300 ml) and extracted with ether. The aqueous layer was acidified with conc. HCl and extracted with ether. The ethereal layer was washed with water, dried (MgSO$_4$) and concentrated to give methyl 2-(carboxy)(phenyl)methylthio-3-(4-methylphenyl)propionate (25.7 g, 90%) as an oil.

NMR(δ ppm in CDCl$_3$): 2.29(3H, s), 2.8–3.2(2H, m), 3.53(3H×½, s), 3.60(3H×½, s), 3.6–3.7(1H, m), 4.72(1H, s), 6.9–7.1(4H, m) 7.2–7.5(5H, m).

REFERENCE EXAMPLE 19

By the same manner as in Reference Example 1, methyl 2-bromo-3-(3,4-ethylenedioxyphenyl)propionate was obtained.

Bp: 170°–173° C./1 mmHg.

NMR(δ ppm in CDCl$_3$): 3.12(1H, double d, J=14 and 7 Hz), 3,36(1H, double d, J=14 and 7 Hz), 3.74(3H, s), 4.24(4H, s), 4.34(1H, t, J=7 Hz), 6.6–6.9(3H, m).

REFERENCE EXAMPLE 20

By the same manner as in Reference Example 1, methyl 2-bromo-3-(2-isopropylphenyl)propionate was obtained.

Bp: 120°–123° C./0.4 mmHg

NMR(δ ppm in CDCl$_3$): 1.24(3H, d, J=7 Hz), 1.25(3H, d, J=7 Hz), 3.1–3.3(1H, m), 3.34(1H, double d, J=14 and 7 Hz), 3.72(3H, s), 4.37(1H, t, J=7 Hz).

REFERENCE EXAMPLE 21

By the same manner as in Reference Example 6, methyl 2-carboxymethylthio-3-(3,4-ethylenedioxyphenyl)propionate was obtained.

NMR(δ ppm in CDCl$_3$) 2.89(1H, double d, J=14 and 7 Hz), 3.12(1H, double d, J=14 and 7 Hz), 3,34(1H, d, J=16 Hz), 3,49(1H, d, J=16 Hz), 3,6–3,8(1H, m), 3.70(3H, s), 4.23(4H, s), 6.6–6.8(3H, m).

REFERENCE EXAMPLE 22

By the same manner as in Reference Example 6, methyl 2-carboxymethylthio-3-(2-isopropylphenyl)propionate was obtained.

NMR(δ ppm in CDCl$_3$): 1.23(3H, d, J=7 Hz), 1.24(3H, d, J=7 Hz), 2.9–3.8(6H, m), 3.67(3H, s), 7.1–7.3(3H, m).

EXAMPLE 1

Oxalyl chloride (11.3 g) and DMF (3 drops) were successively added dropwise to a solution of 2-(carboxy)(phenyl)methylthio-3-(4-methylphenyl)propionate (25.5 g) in tetrahydrofuran (THF) (150 ml), followed by stirring for 1.5 hours at room temperature and concentrated under reduced pressure. The residual oil was dissolved in dichloromethane (50 ml). The solution was added dropwise to a suspension of aluminum chloride (AlCl$_3$)(21.7 g) and dichloromethane (200 ml) with ice-cooling. The reaction mixture was stirred for 2 hours with ice-cooling and poured into ice-water. The dichloromethane layer was separated, washed with water, dried (MgSO$_4$) and distilled off to give crystals of methyl trans-7-methyl-5-oxo-4-phenyl-1,2,4,5-tetrahydro-3-benzothiepine-2-carboxylate (7.2 g, 30%). Recrystallization from ethyl acetate-hexane gave colorless prisms.

mp: 136°–137° C.

Elementary Analysis for C$_{19}$H$_{18}$O$_3$S

Calc.: C, 69.91; H, 5.56.
Found: C, 69.93; H, 5.53.

EXAMPLES 2-6

Compounds listed in Table 6 were obtained by the same manner as in Example 1.

EXAMPLE 7

Oxalyl chloride (14.8 g) and DMF (3 drops) were successively added dropwise to a solution of methyl 2-carboxymethylthio-3-(3,4-methylenedioxyphenyl)-propionate (29.0 g) in tetrahydrofuran (THF) (200 ml), followed by stirring for 1.5 hours at room temperature and concentrated under reduced pressure. The residual oil was dissolved in dichloromethane (250 ml). To the solution was added dropwise tin(IV) chloride (SnCl$_4$)(55.6 g) under ice-cooling. The mixture was stirred for an hour under ice-cooing, to which 2NHCl (100 ml) was added dropwise. The dichloromethane layer was separated, washed with water, dried (MgSO$_4$) and distilled off the solvent to give crystals of methyl 7,8-methylenedioxy-5-oxo-1,2,4,5-tetrahydro-3-benzothiepine-2-carboxylate (17.0 g, 63%). Recrystallization from ethyl acetate gave colorless prisms.

mp: 165°–166° C.

Elementary Analysis for C$_{13}$H$_{12}$O$_5$S

Calc.: C, 55.71; H, 4.32.
Found: C, 55.69; H, 4.37.

EXAMPLE 8

By the same manner as in Example 7, methyl 7,8-dimethoxy-5-oxo-1,2,4,5-tetrahydro-3-benzothiepine-2-carboxylate was obtained as an oil.

Yield: 65%.

NMR(δ ppm in CDCl$_3$) 3.18(1H, double d, J=15 and 5 Hz), 3.41(1H, d, J=18 Hz), 3.5(1H, m),3.70(1H, double d, J=15 and 5 Hz), 3.81(3H, s), 3.93(3H, s), 3.95(3H, s), 3.95 (1H, d, J=18 Hz), 6.71(1H, s), 7.51(1H, m).

EXAMPLE 9

Oxalyl chloride (13.6 g) and DMF (3 drops) were successively added dropwise to a solution of methyl 2-(1-carboxyethyl)thio-3-(3,4-methylenedioxyphenyl)-propionate (27.8 g) in tetrahydrofuran (THF) (200 ml), followed by stirring for 1.5 hours at room temperature and concentrated under reduced pressure. The residual oil was dissolved in dichloromethane (250 ml). To the solution was added dropwise tin(IV) tetrachloride (SnCl$_4$)(51.0 g) under ice-cooling. The mixture was stirred for an hour under ice-cooing, to which 2NHCl (100 ml) was added dropwise. The dichloromethane layer was separated, washed with water, dried (MgSO$_4$) and distilled off the solvent. The residual oil was dissolved in methanol (250 ml), to which a solution of sodium methoxide in methanol (28%, 10 ml) was added. The resultant solution was stirred for 1.5 hours at room temperature to which 2N—HCl (250 ml) was added. The precipitated crystals were collected by filtration to give methyl trans-7,8-methylenedioxy-4-methyl-5-oxo-1,2,4,5-tetrahydro-3-benzothiepine-2-carboxylate (19.0 g, 73%). Recrystallization from ethyl acetate gave colorless prisms.

mp: 171°–172° C.

Elementary Analysis for $C_{14}H_{14}O_5S$

Calc.: C, 57.13; H, 4.79.
Found: C, 57.19; H, 4.90.

EXAMPLE 10

Thionyl chloride (16.4 g) and pyridine (3 drops) were successively added dropwise to a solution of methyl 2-(1-carboxyethyl)thio-3-(3,4-methylenedioxyphenyl)-propionate (26.0 g) in ether (250 ml), followed by stirring for an hour at room temperature and for an hour under reflux. The mixture was concentrated under reduced pressure. The residual oil was dissolved in dichloromethane (50 ml) and the resultant solution was added dropwise to a mixture of aluminum chloride ($AlCl_3$)(27.0 g) and dichloromethane (200 ml) under ice-cooling. After stirring for two hours under ice-cooling, the mixture was poured into ice-water. The dichloromethane layer was separated, washed with water, dried ($MgSO_4$) and distilled to remove the solvent. The residual oil was dissolved in methanol (250 ml), to which a solution of sodium methoxide in methanol (28%, 10 ml) was added. The mixture was stirred for 1.5 hours at room temperature, to which 2N—HCl (250 ml) was added. The precipitated crystals was collected by filtration, affording methyl trans-4,7-dimethyl-5-oxo-1,2,4,5-tetrahydro-3-benzothiepine-2-carboxylate (15.0 g, 62%). Recrystallization from ethyl acetate-hexane gave colorless prisms.

mp: 99°–100° C.

Elementary Analysis for $C_{14}H_{16}O_3S$

Calc.: C, 63.61; H, 6.10.
Found: C, 63.38; H, 6.22.

EXAMPLE 11

By the same manner as in Example 10, methyl trans-4-methyl-8-methylthio-5-oxo-1,2,4,5-tetrahydro-3-benzothiepine-2-carboxylate was obtained as crystals. Recrystallization from ethyl acetate-hexane gave colorless prisms.

mp: 105°–106° C.

Elementary Analysis for $C_{14}H_{16}O_3S_2$

Calc.: C, 56.73; H, 5.44.
Found: C, 56.91; H, 5.46.

EXAMPLE 12

Methyl 7,8-methylenedioxy-5-oxo-1,2,4,5-tetrahydro-3-benzothiepine-2-carboxylate (16.5 g) was suspended in methanol (100 ml), to which 2N—KOH (100 ml) was added. After stirring for an hour at room temperature, the mixture was poured into water, acidified and then extracted with ethyl acetate. The ethyl acetate layer was washed with water, dried ($MgSO_4$) and concentrated to afford 7,8-methylenedioxy-5-oxo-1,2,4,5-tetrahydro-3-benzothiepine-2-carboxylic acid (13.5 g, 86%). Recrystallization from ethyl acetate gave colorless prisms.

mp: 234°–235° C.

Elementary Analysis for $C_{12}H_{10}O_5S$

Calc.: C, 54.13; H, 3.79.
Found: C, 54.16; H, 3.81.

EXAMPLES 13 TO 22

Compounds listed in Table 7 were obtained by the same manner as in Example 12.

EXAMPLE 23

To a solution of 7,8-dimethoxy-5-oxo-1,2,4,5-tetrahydro-3-benzothiepine-2-carboxylic acid (0.9 g) in tetrahydrofuran (THF) (30 ml) were added oxalyl chloride (0.445 g) and DMF (one drop) successively. The reaction mixture was stirred for 3 hours at room temperature and concentrated under reduced pressure. The residual oil was dissolved in dichloromethane (10 ml). The solution was added dropwise to a mixture of diethyl 4-aminophenylphosphonate (0.733 g), potassium carbonate (3 g) and dichloromethane (30 ml) at room temperature, followed by stirring for 30 minutes at room temperature. The reaction mixture was washed successively with water, 2N—HCl and water and dried ($MgSO_4$). The solvent was distilled off under reduced pressure to obtain N-(4-diethoxyphosphorylphenyl)-7,8-dimethoxy-5-oxo-1,2,4,5-tetrahydro-3-benzothiepine-2-carboxamide (1.25 g, 78%) as crystals. Recrystallization from ethyl acetate-hexane gave colorless prisms.

mp: 171°–172° C.

Elementary Analysis for $C_{23}H_{28}NO_7PS$

Calc.: C, 55.98; H, 5.72; N, 2.84.
Found: C, 55.90; H, 5.82; N, 2.73.

EXAMPLES 24 TO 25

Compounds listed in Table 8 were obtained by the same manner as in Example 23.

EXAMPLE 26

To a solution of 7-chloro-5-oxo-1,2,4,5-tetrahydro-3-benzothiepine-2-carboxylic acid (0.9 g) in ether (10 ml) were added thionyl chloride (0.626 g) and pyridine (one drop) successively. The mixture was refluxed for 1 hour and concentrated under reduced pressure. The residual oil was dissolved in dichloromethane (10 ml). The resultant solution was added dropwise to a mixture of 4-chloroaniline (0.447 g), potassium carbonate (3 g) and dichloromethane (20 ml) at room temperature, followed by stirring for 30 minutes at room temperature. The reaction mixture was washed successively with water, 2N—HCl and water and dried ($MgSO_4$). The solvent was distilled off under reduced pressure to obtain 7-chloro-N-(4-chlorophenyl)-5-oxo-1,2,4,5-tetrahydro-3-benzothiepine-2-carboxamide (0.76 g, 58%) as crystals. Recrystallization from ethanol gave colorless needles.

mp: 235°–236° C.

Elementary Analysis for $C_{17}H_{13}NO_2Cl$

Calc.: C, 55.75; H, 3.58; N, 3.82.
Found: C, 55.67; H, 3.52; N, 3.79.

EXAMPLES 27 TO 45

Compounds listed in Table 9 were obtained by the same manner as in Example 26.

EXAMPLE 46

To a solution of 7,8-methylenedioxy-5-oxo-1,2,4,5-tetrahydro-3-benzothiepine-2-carboxylic acid (1.07 g) in tetrahydrofuran (20 ml) were added oxalyl chloride (0.609 g) and DMF (one drop) successively. The mixture was stirred for 3 hours at room temperature and concentrated under reduced pressure. The residual oil was dissolved in dichloromethane (10 ml). The solution was added dropwise to a mixture of diethyl 4-aminobenzylphosphonate (1.07 g), sodium hydrogen carbonate (3 g) and dichloromethane (30 ml) at room temperature, followed by stirring for 30 minutes at room temperature. The reaction mixture was washed successively with water, 2N—HCl and water and dried (MgSO$_4$). The solvent was distilled off under reduced to obtain N-(4-diethoxphosphorylmethylphenyl)-7,8-methylenedioxy-5-oxo-1,2,4,5-tetrahydro-3-benzothiepine-2-carboxamide (1.6 g, 81%) as crystals. Recrystallization from ethanol-chloroform gave colorless prisms.

mp: 192°–193° C.
Calc.: C, 56.21; H, 5.33; N, 2.85.
Found: C, 56.12; H, 5.34; N, 2.73.

EXAMPLES 47 TO 59

Compounds listed in Table 10 were obtained by the same manner as in Example 46.

EXAMPLE 60

To a solution of 8-methylthio-5-oxo-1,2,4,5-tetrahydro-3-benzothiepine-2-carboxylic acid (1.1 g) in tetrahydrofuran (20 ml) were added oxalyl chloride (0.609 g) and DMF (one drop) successively. The mixture was stirred for 3 hours at room temperature and concentrated under reduced pressure. The residual oil was dissolved in dichloromethane (10 ml). The solution was added dropwise to a mixture of ethyl 4-aminobenzoate (0.722 g), triethylamine (2 g) and dichloromethane (30 ml) at room temperature, followed by stirring for 30 minutes at room temperature. The reaction mixture was washed successively with water, 2N—HCl and water and dried (MgSO$_4$). The solvent was distilled off under reduced pressure to obtain N-(4-ethoxycarbonylphenyl)-8-methylthio-5-oxo-1,2,4,5-tetrahydro-3-benzothiepine-2-carboxamide (1.2 g, 71%) as crystals. Recrystallization from ethyl acetate gave colorless needles.

mp: 236°–237° C.

Elementary Analysis for $C_{22}H_{26}NO_5PS_2$

Calc.: C, 55.10; H, 5.46; N, 2.92.
Found: C, 54.94; H, 5.50; N, 2.84.

EXAMPLES 61 TO 68

Compounds listed in Table 11 were obtained by the same manner as in Example 60.

EXAMPLE 69

To a solution of trans-N-(4-diethoxyphosphorylmethylphenyl)-7,8-methylenedioxy-4-methyl-5-oxo-1,2,4,5-tetrahydro-3-benzothiepine-2-carboxamide (0.506 g) in chloroform (10 ml) was added dropwise a solution of m-chloroperbenzoic acid (85%, 0.487 g) in chloroform (10 ml) under ice-cooling. The reaction mixture was allowed to stand overnight at room temperature, washed successively with aqueous saturated sodium hydrogen carbonate and water and then dried (MgSO$_4$). The solvent was distilled off under reduced pressure to obtain trans-N-(4-diethoxyphosphorylmethylphenyl)-7,8-methylenedioxy-4-methyl-5-oxo-1,2,4,5-tetrahydro-3-benzothiepine-2-carboxamide 3,3-dioxide (0.48 g, 89%). Recrystallization from ethanol-chloroform gave colorless prisms.

mp: 242°–243° C.

Elementary Analysis for $C_{24}H_{28}NO_9PS$

Calc. C, 53.63; H, 5.25; N, 2.61.
Found: C, 53.34; H, 5.12; N, 2.49.

EXAMPLE 70

By the same manner as in Example 69, N-(4-chlorophenyl)-7,8-methylenedioxy-5-oxo-1,2,4,5-tetrahydro-3-benzothiepine-2-carboxamide 3,3-dioxide (92%) was obtained as crystals. Recrystallization from ethyl acetate gave colorless prisms.

mp: 240°–241° C.

Elementary Analysis for $C_{19}H_{16}NO_6SCl$

Calc.: C, 54.10; H, 3.82; N, 3.32.
Found: C, 54.17; H, 3.91; N, 3.26.

EXAMPLE 71

To a solution of trans-N-(4-ethoxycarbonylphenyl)-7,8-methylenedioxy-4-methyl-5-oxo-1,2,4,5-tetrahydro-3-benzothiepine-2-carboxamide (0.428 g) in chloroform (10 ml) was added dropwise a solution of m-chloroperbenzoic acid (85%, 0.203 g) in chloroform (10 ml) under ice-cooling. The reaction mixture was washed successively with aqueous saturated sodium hydrogen carbonate and water and dried (MgSO$_4$). The solvent was distilled off under reduced pressure to obtain N-(4-ethoxycarbonylphenyl)-7,8-methylenedioxy-t-4-methyl-5-oxo-1,2,4,5-tetrahydro-3-benzothiepine-r-2-carboxamide 3-oxide (0.405 g, 91%) as a mixture of 2,3-cis and 2,3-trans. Recrystallization from ethyl acetate-hexane gave colorless needles.

mp: 217°–218° C.

Elementary Analysis for $C_{22}H_{21}NO_7S$

Calc.: C, 59.58; H, 4.77; N, 3.16.
Found: C, 59.56; H, 4.74; N, 3.25.

EXAMPLE 72

By the same manner as in Example 1, methyl 9-isopropyl-5-oxo-1,2,4,5-tetrahydro-3-benzothiepine-2-carboxylate was obtained. Recrystallization from ethyl acetate-hexane gave colorless needles.

mp 116°–117° C.

Elementary Analysis for $C_{15}H_{18}O_3S$

Calc.: C, 64.72; H, 6.52.
Found: C, 64.58; H, 6.58.

EXAMPLE 73

By the same manner as in Example 7, methyl 7,8-ethylenedioxy-5-oxo-1,2,4,5-tetrahydro-3-benzothiepine-2-carboxylate was obtained. Recrystallization from ethyl acetate gave colorless prisms.

mp: 181°–182° C.

Elementary Analysis for $C_{14}H_{14}O_5S$

Calc.: C, 57.13; H, 4.79.
Found: C, 57.06; H, 4.78.

EXAMPLE 74

By the same manner as in Example 12, 9-isopropyl-5-oxo-1,2,4,5-tetrahydro-3-benzothiepine-2-carboxylic acid was obtained. Recrystallization from ethyl acetate-hexane gave colorless prisms.

mp: 157°–158° C.

Elementary Analysis for $C_{14}H_{16}O_3S$

Calc. C, 63.61; H, 6.10.
Found: C, 63.55; H, 6.12.

EXAMPLE 75

By the same manner as in Example 12, 7,8-ethylenedioxy-5-oxo-1,2,4,5-tetrahydro-3-benzothiepine-2-carboxylic acid was obtained. Recrystallization from ethyl acetate gave colorless prisms.
mp: 208°–209° C.

Elementary Analysis for $C_{13}H_{12}O_5S$

Calc.: C, 55.71; H, 4.32.
Found: C, 55.74; H, 4.49.

EXAMPLE 76–81

By the same manner as in Example 26, compounds listed in Table 12 were obtained.

EXAMPLE 82

By the same manner as in Example 69, N-(4-chlorophenyl)-7,8-ethylenedioxy-5-oxo-1,2,4,5-tetrahydro-3-benzothiepine-2-carboxamide 3,3-dioxide was obtained. Recrystallization from chloroform-methanol gave colorless prisms.
mp: 273°–274° C.

Elementary Analysis for $C_{19}H_{16}O_6S$

Calc.: C, 54.10; H, 3.82; N, 3.32.
Found: C, 54.11; H, 3.89; N, 3.34.

EXAMPLE 83

By the same manner as in Example 69, N-(4-diethoxyphosphorylmethylphenyl)-7,8-ethylenedioxy-5-oxo-1,2,4,5-tetrahydro-3-benzothiepine-2-carboxamide 3,3-dioxide was obtained. Recrystallization from ethanol gave colorless plates.
mp: 198°–199° C.

Elementary Analysis for $C_{24}H_{28}NO_9PS$

Calc.: C, 53.63; H, 5.25; N, 2.61.
Found: C, 53.11; H, 5.49; N, 2.38.

EXAMPLE 84

By the same manner as in Example 69, N-(4-chlorophenyl)-9-isopropyl-5-oxo-1,2,4,5-tetrahydro-3-benzothiepine-2-carboxamide 3,3-dioxide was obtained. Recrystallization from ethyl acetate-hexane gave colorless prisms.
mp: 241°–242° C.

Elementary Analysis for $C_{20}H_{20}NO_4SCl$

Calc C, 59.18; H, 4.97; N, 3.45.
Found: C, 59.05; H, 5.06; N, 3.41.

EXAMPLE 85

By the same manner as in Example 69, N-(4-diethoxyphosphorylphenyl)-9-isopropyl-5-oxo-1,2,4,5-tetrahydro-3-benzothiepine-2-carboxamide 3,3-dioxide was obtained. Recrystallization from ethanol gave colorless prisms.
mp: 229°–230° C.

Elementary Analysis for $C_{24}H_{30}NO_7PS$

Calc. C, 56.80; H, 5.96; N, 2.76.
Found: C, 56.60; H, 6.18; N, 2.85.

EXAMPLE 86

By the same manner as in Example 69, N-(4-chlorophenyl)-5-oxo-1,2,4,5-tetrahydro-3-benzothiepine-2-carboxamide 3,3-dioxide was obtained. Recrystallization from chloroform-methanol gave colorless prisms.
mp: 212°–213° C.

Elementary Analysis for $C_{17}H_{14}NO_4SCl$

Calc.: C, 56.12; H, 3.88; N, 3.85.
Found: C, 56.30; H, 3.95; N, 3.79.

EXAMPLE 87

Sodium borohydride (22 mg) was added to a mixture of N-(4-diethoxyphosphorylmethylphenyl)-7,8-ethylenedioxy-5-oxo-1,2,4,5-tetrahydro-3-benzothiepine-2-carboxamide 3,3-dioxide (300 mg) and ethanol (20 ml) under ice-cooling, followed by stirring for 30 minutes. To the resultant mixture was added acetic acid (0.1 ml). The reaction mixture was poured into water and extracted with ethyl acetate. The ethyl acetate layer was washed with water, dried (MgSO$_4$) and concentrated under reduced pressure to give a mixture of 2,5-cis and 2,5-trans forms of N-(4-diethoxyphosphorylmethylphenyl)-7,8-ethylenedioxy-5-hydroxy-1,2,4,5-tetrahydro-3-benzothiepine-2-carboxamide 3,3-dioxide (270 mg, 90%). Recrystallization from chloroform gave colorless prisms.
mp: 257°–258° C.

Elementary Analysis for $C_{24}H_{30}NO_9PS$

Calc.: C, 53.43; H, 5.60; N, 2.60.
Found: C, 53.27; H, 5.70; N, 2.59.

EXAMPLE 88

By the same manner as in Example 87, a mixture of 2,5-cis and trans forms of N-(4-chlorophenyl)-7,8-ethylenedioxy-5-hydroxy-1,2,4,5-tetrahydro-3-benzothiepine-2-carboxamide 3,3-dioxide was obtained. Recrystallization from chloroform-methanol gave colorless prisms.
mp: 292°–293° C.

Elementary Analysis for $C_{19}H_{18}NO_6SCl$

Calc C, 53.84; H, 4.28; N, 3.30.
Found: C, 53.80; H, 4.41; N, 3.59.

EXAMPLE 89

By the same manner as in Example 87, a mixture of 2,5-cis and trans forms of N-(4-chlorophenyl)-5-hydroxy-7,8-methylenedioxy-1,2,4,5-tetrahydro-3-benzothiepine-2-carboxamide was obtained. Recrystallization from chloroform-methanol gave colorless prisms.
mp: 228°–229° C.

Elementary Analysis for $C_{18}H_{16}NO_4SCl$

Calc.: C, 57.22; H, 4.27; N, 3.71.
Found: C, 57.55; H, 4.33; N, 3.65.

PREPARATION EXAMPLE 1

| Components of a tablet | |
|---|---|
| (1) Compound of Example 30 | 50.0 mg |
| (2) Cornstarch | 30.0 mg |
| (3) Lactose | 113.4 mg |
| (4) Hydroxypropyl cellulose | 6.0 mg |
| (5) Water | (0.03 ml) |
| (6) Magnesium stearate | 0.6 mg |

-continued

| Components of a tablet | |
|---|---|
| Total | 200.0 mg |

The components (1), (2), (3) and (4) were mixed. After adding water, the mixture was kneaded, dried under vacuum for 16 hours at 40° C. and grounded in a mortar. The resultant was sieved through a 16-mesh sieve to obtain granules. The component (6) was added to the granules and mixed. The resulting mixture was made to tablets of 200 mg per tablet, using a rotary-type tablet machine (Kikusui Seisakusho in Japan).

PREPARATION EXAMPLE 2

| (1) Compound of Example 24 | 50.0 mg |
|---|---|
| (2) Cornstarch | 30.0 mg |
| (3) Lactose | 113.4 mg |
| (4) Hydroxypropyl cellulose | 6.0 mg |
| (5) Water | (0.03 ml) |
| (6) Magnesium stearate | 0.6 mg |
| (7) Cellulose acetate phthalate | 10.0 mg |
| (8) Acetone | (0.2 ml) |
| Total | 210.0 mg |

From the components (1), (2), (3), (4), (5) and (6), tablets were prepared by the same method as in Preparation Example 1. These tablets were film-coated by use of a solution of the component (7) in acetone in a half coater (Freund Co., Ltd.) to give enteric coated tablets of 210mg per tablet.

PREPARATION EXAMPLE 3

| Component of a capsule | |
|---|---|
| (1) Compound of Example 27 | 30.0 mg |

-continued

| Component of a capsule | |
|---|---|
| (2) Cornstarch | 40.0 mg |
| (3) Lactose | 74.0 mg |
| (4) Hydroxypropyl cellulose | 6.0 mg |
| (5) Water | (0.02 ml) |
| Total | 150.0 mg |

The components (1), (2), (3) and (4) were mixed, to which water was added. The mixture was kneaded, dried under vacuum for 16 hours at 40° C. and grounded in a mortar. The resultant was sieved through a 16-mesh sieve to give granules. The granules were packed in No. 3 gelatin capsules with a capsule packing machine (Zanassi Italy) to obtain capsules.

PREPARATION EXAMPLE 4

| Component of a capsule | |
|---|---|
| (1) Compound of Example 35 | 5.0 mg |
| (2) Sodium salicylate | 50.0 mg |
| (3) Sodium chloride | 180.0 mg |
| (4) Sodium metabisulfite | 20.0 mg |
| (5) Methylparaben | 36.0 mg |
| (6) Propylparaben | 4.0 mg |
| (7) Distilled water for injection | (2.0 ml) |
| Total | 295.0 mg |

The components (2), (3), (4), (5) and (6) were dissolved in about one half of the above-mentioned volume of distilled water under stirring at 80° C. The solution thus obtained was cooled to 40° C., to which the compound of the present invention was dissolved. The remaining distilled water was added to the solution so that a final volume can be obtained. The resultant was sterilized through an appropriate filter paper, to give the injection.

TABLE 4

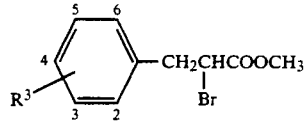

| Ref. Ex. No. | $R^3$ | Yield (%) | Boiling Point (°C./mmHg) | NMR (δ ppm in CDCl$_3$) |
|---|---|---|---|---|
| 2 | 4-CH$_3$ | 81 | 129-133/2 | 2.32(3H, s), 3.20(1H, double d, $J$=14 and 7Hz), 3.43(1H, double d, J=14 and 7Hz), 3.73(3H, s), 4.38(1H, t, $J$=7Hz), 7.10(4H, s) |
| 3 | 3,4-(CH$_3$)$_2$ | 72 | 120-124/0.5 | 2.23(6H, s), 3.16(1H, double d, $J$=14 and 7Hz), 3.42(1H, double d, J=14 and 7Hz), 3.73(3H, s), 4.38(1H, t, $J$=7Hz), 6.9~7.1(3H, m) |
| 4 | 3,4-(CH$_3$O)$_2$ | 75 | 142-145/0.5 | 3.18(1H, double d, $J$=14 and 7Hz), 3.41(1H, double d, $J$=14 and 9 Hz), 3.73(3H, s), 3.86(3H, s), 3.87(3H, s), 4.37(1H, double d, $J$=9 and 7Hz), 6.7-6.9(3H, m) |
| 5 | 3-CH$_3$S | 45 | 151-153/1 | 2.48(3H, s), 3.20(1H, double d, $J$=14 and 7Hz), 3.44(1H, double d, $J$=14 and 7Hz), 3.74(3H, s), 4.39(1H, d, $J$=7Hz), 6.9-7.3(4H, m) |

TABLE 5

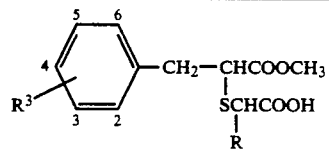

| Ref. Ex. No. | $R^3$ | R | Yield (%) | NMR(δ ppm in CDCl$_3$) |
|---|---|---|---|---|
| 7 | 4-Cl | H | 85 | 2.9~3.8(5H, m), 3.69(3H, s), 7.1~7.3(4H, m) |
| 8 | 4-CH$_3$ | H | 90 | 2.31(3H, s), 2.96(1H, double d, $J$=14 and 7Hz), 3.18(1H, double d, $J$=14 and 9Hz), 3.35(1H, d, $J$=16Hz), 3.49(1H, d, $J$=16Hz), 3.68(3H, s), 3.7-3.8 |

TABLE 5-continued

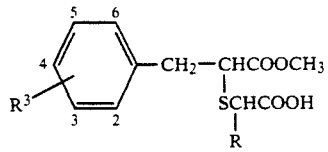

| Ref. Ex. No. | R³ | R | Yield (%) | NMR(δ ppm in CDCl₃) |
|---|---|---|---|---|
| 9 | 4-CH₃ | CH₃ | 94 | (1H, m), 7.09(4H, s)<br>1.45(3H, m), 2.31(3H, s), 2.9–3.3(2H, m), 3.4~3.9(3H, m), 3.66(3H, s), 7.09(4H, s) |
| 10 | 3,4-(CH₃)₂ | H | 89 | 2.22(6H, s), 2.93(1H, double d, $\underline{J}$=14 and 7Hz), 3.19(1H, double d, $\underline{J}$=14 and 9Hz), 3.35(1H, d, $\underline{J}$=16Hz), 3.49(1H, d, $\underline{J}$=16Hz), 3.68(3H, s), 3.7–3.8 (1H, m), 6.9–7.1(3H, m) |
| 11 | 3,4-(CH₃O)₂ | H | 64 | 2.94(1H, double d, $\underline{J}$=14 and 7Hz), 3.17(1H, double d, $\underline{J}$=14 and 9Hz), 3.35(1H, d, $\underline{J}$=16Hz), 3.49(1H, d, $\underline{J}$=16Hz), 3.68(3H, s), 3.7–3.8(1H, m), 3.85(3H, s), 3.86(3H, s), 6.7–6.8(3H, m) |
| 12 | 3,4-OCH₂O— | CH₃ | 97 | |
| 13 | 3-CH₃S | H | 97 | |
| 14 | 3-CH₃S | CH₃ | quantitative | 1.44(3H×½, d, $\underline{J}$=7Hz), 1.45(3H×½, d, $\underline{J}$=7Hz), 2.47(3H, s), 2.9~3.3 (2H, m), 3.5~3.9(3H, m), 3.67(3H×½, s), 3.70(3H×½, s), 6.9~7.3(4H, m) |
| 15 | H | H | quantitative | 3.00(1H, double d, $\underline{J}$=14 and 7Hz), 3.23(1H, double d, $\underline{J}$=14 and 9Hz), 3.35 (1H, d, $\underline{J}$=16Hz), 3.50(1H, d, $\underline{J}$=16Hz), 3.68(3H, s), 3.74(1H, double d, $\underline{J}$=9 and 7Hz), 7.1–7.45(5H, m) |

TABLE 6

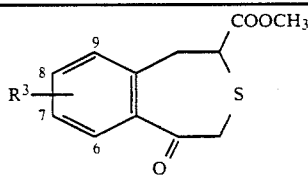

| Example No. | R³ | Yield (%) | Melting Point (°C.) | Solvent for Recrystallization |
|---|---|---|---|---|
| 2 | 7-Cl | 37 | 130–131 | ethyl acetate-hexane |
| 3 | 7,8-(CH₃)₂ | 81 | 160–161 | ethyl acetate |
| 4 | 8-CH₃S | 65 | 122–123 | ethyl acetate-hexane |
| 5 | 7-CH₃ | 75 | 119–120 | ethyl acetate |
| 6 | H | 83 | oil Note 1) | |

Note 1)
NMR(δ ppm in CDCl₃): 3.23(1H, double d, $\underline{J}$=14 and 5Hz), 3.41(1H, d, $\underline{J}$=18Hz), 3.4~3.8(2H, m), 3.82(3H, s), 4.02(1H, d, $\underline{J}$=18Hz), 7.2–7.6(3H, m), 7.91(1H, double d, $\underline{J}$=9 and 2Hz)

TABLE 7

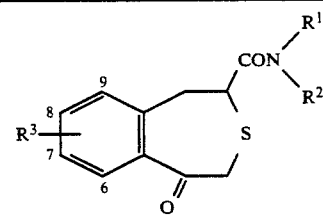

| Example No. | R³ | R | Yield (%) | Melting Point (°C.) | Solvent for Recrystallization |
|---|---|---|---|---|---|
| 13 | 7-Cl | H | 91 | 201–202 | ethyl acetate |
| 14 | 7-CH₃ | H | 92 | 205–206 | ethyl acetate |
| 15 | 7-CH₃ | CH₃ | 84 | 193–194 | ethyl acetate |
| 16 | 7-CH₃ | 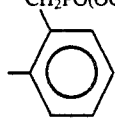 | 64 | 196–197 | ethyl acetate |
| 17 | 7,8-(CH₃)₂ | H | 78 | 243–244 | acetone |
| 18 | 7,8-(CH₃O)₂ | H | 89 | 244–245 | ethyl acetate |
| 19 | 7,8-OCH₂O— | CH₃ | 86 | 219–220 | ethyl acetate |
| 20 | 8-CH₃S | H | 87 | 217–218 | ethyl acetate |
| 21 | 8-CH₃S | CH₃ | 71 | 183–184 | methanol |
| 22 | H | H | 71 | 215–216 | ethyl acetate |

TABLE 8

| Example No. | R³ | R¹ | R² | Yield (%) | Melting Point (°C.) | Solvent for Recrystallization |
|---|---|---|---|---|---|---|
| 24 | 7,8-(CH₃O)₂ | CH₂PO(OC₂H₅)₂ | H | 81 | 135–136 | ethyl acetate-hexane |

TABLE 8-continued

[Structure: benzothiepine with R³ substituent on aromatic ring (positions 6,7,8,9), CON(R¹)(R²) group, and C=O]

| Example No. | R³ | R¹ | R² | Yield (%) | Melting Point (°C.) | Solvent for Recrystallization |
|---|---|---|---|---|---|---|
| 25 | 7,8-(CH₃O)₂ | [2-(phenyl)-1-(isopropylideneamino)vinyl-thio group: CH₃-C(=N-)-S-C(Ph)=CH-] | H | 51 | 227–228 | ethyl acetate-hexane |

TABLE 9

[Structure: benzothiepine with R³ on aromatic ring, CON(R¹)(R²) group, and C(=O)-CHR]

| Example No. | R³ | R | R¹ | R² | Yield (%) | Melting Point (°C.) | Solvent for Recrystallization |
|---|---|---|---|---|---|---|---|
| 27 | 7-Cl | H | —C₆H₄—CH₂PO(OC₂H₅)₂ | H | 58 | 240–241 | ethanol - chloroform |
| 28 | 7-CH₃ | H | —C₆H₄—Cl | H | 79 | 226–227 | ethyl acetate |
| 29 | 7-CH₃ | H | —C₆H₄—CH₂PO(OC₂H₅)₂ | H | 89 | 232–233 | ethanol - chloroform |
| 30 | 7-CH₃ | H | —C₆H₄—PO(OC₂H₅)₂ | H | 78 | 211–212 | ethanol |
| 31 | 7-CH₃ | H | 2-(phenyl)-1-(isopropylideneamino)vinylthio group | H | 44 | 228–229 | ethyl acetate |
| 32 | 7-CH₃ | H | —CH₂—C₆H₅ | CH₃ | 86 | 165–166 | ethyl acetate |
| 33 | 7-CH₃ | CH₃ | —C₆H₄—Cl | H | 60 | 215–216 | ethyl acetate |

TABLE 9-continued

[Structure: bicyclic benzothiepine core with R³ substituent on benzene ring (positions 6,7,8,9), ketone (C=O), sulfur in ring, R substituent, and CONR¹R² side chain]

| Example No. | R³ | R | R¹ | R² | Yield (%) | Melting Point (°C.) | Solvent for Recrystallization |
|---|---|---|---|---|---|---|---|
| 34 | 7-CH₃ | CH₃ | (4-CH₂PO(OC₂H₅)₂-phenyl) | H | 79 | 228–229 | ethyl acetate |
| 35 | 7,8-(CH₃)₂ | H | (4-Cl-phenyl) | H | 71 | 256–257 | ethyl acetate |
| 36 | 7,8-(CH₃)₂ | H | (4-PO(OC₂H₅)₂-phenyl) | H | 39 | 203–204 | ethanol |
| 37 | 7,8-(CH₃)₂ | H | (4-CH₂PO(OC₂H₅)₂-phenyl) | H | 63 | 215–216 | ethanol - chloroform |
| 38 | 7,8-(CH₃)₂ | H | —CH₂-phenyl | CH₃ | 71 | 133–134 | ethyl acetate |
| 39 | 7,8-(CH₃)₂ | H | —CH₂CH₂-(3,4-di-OCH₃-phenyl) | CH₃ | 55 | 147–148 | ethyl acetate - hexane |
| 40 | 7,8-(CH₃)₂ | H | (3-pyridyl-CH₂) | H | 32 | 206–207 | ethanol |
| 41 | 7,8-(CH₃O)₂ | H | (4-CH₂PO(OC₂H₅)₂-phenyl) | H | 75 | 217–218 | ethanol - chloroform |
| 42 | 7,8-(CH₃O)₂ | H | (4-Cl-phenyl) | H | 63 | 192–193 | ethanol |
| 43 | 7,8-(CH₃O)₂ | H | cyclohexyl | H | 30 | 118–119 | ethyl acetate - hexane |
| 44 | 7,8-(CH₃O)₂ | H | (3-pyridyl) | H | 36 | 212–213 | ethanol |

TABLE 9-continued

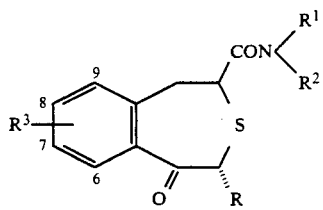

| Example No. | R³ | R | R¹ | R² | Yield (%) | Melting Point (°C.) | Solvent for Recrystallization |
|---|---|---|---|---|---|---|---|
| 45 | 7,8-(CH₃O)₂ | H | —CH₂CH₂—(C₆H₃)(OCH₃)(OCH₃) | CH₃ | 23 | 139–140 | ethyl acetate - hexane |

TABLE 10

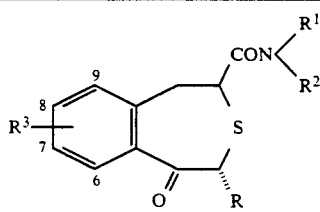

| Example No. | R³ | R | R¹ | R² | Yield (%) | Melting Point (°C.) | Solvent for Recrystallization |
|---|---|---|---|---|---|---|---|
| 47 | 7,8-OCH₂O— | H | —C₆H₄—PO(OC₂H₅)₂ | H | 63 | 199–200 | ethanol |
| 48 | 7,8-OCH₂O— | CH₃ | —C₆H₄—CH₂PO(OC₂H₅)₂ | H | 95 | 218–219 | ethanol - chloroform |
| 49 | 7,8-OCH₂O— | CH₃ | —C₆H₄—PO(OC₂H₅)₂ | H | 60 | 185–186 | ethanol |
| 50 | 7,8-OCH₂O— | CH₃ | —C₆H₄—Cl | H | 91 | 261–262 | ethyl acetate |
| 51 | 7,8-OCH₂O— | CH₃ | —C₆H₄—COOC₂H₅ | H | 88 | 243–244 | ethyl acetate |
| 52 | 7-CH₃ | —C₆H₅ | —C₆H₄—CH₂PO(OC₂H₅)₂ | H | 56 | 198–199 | methanol |
| 53 | 7-CH₃ | —C₆H₅ | —C₆H₄—Cl | H | 56 | 222–223 | ethyl acetate |

TABLE 10-continued

[Structure: bicyclic compound with R³ substituent on benzene ring (positions 6,7,8,9), S in ring, C=O, R substituent, and CONR¹R² group]

| Example No. | R³ | R | R¹ | R² | Yield (%) | Melting Point (°C.) | Solvent for Recrystallization |
|---|---|---|---|---|---|---|---|
| 54 | 8-CH$_3$S | CH$_3$ | –C$_6$H$_4$–CH$_2$PO(OC$_2$H$_5$)$_2$ | H | 61 | 211–212 | chloroform - ethanol |
| 55 | 8-CH$_3$S | CH$_3$ | –C$_6$H$_4$–PO(OC$_2$H$_5$)$_2$ | H | 57 | 214–215 | chloroform - ethanol |
| 56 | 8-CH$_3$S | CH$_3$ | –C$_6$H$_4$–Cl | H | 41 | 249–250 | chloroform - ethanol |
| 57 | 8-CH$_3$S | CH$_3$ | –C$_6$H$_4$–COOC$_2$H$_5$ | H | 49 | 221–222 | chloroform - ethanol |
| 58 | 8-CH$_3$S | CH$_3$ | pyridyl | H | 16 | 213–214 | ethyl acetate - hexane |
| 59 | 8-CH$_3$S | CH$_3$ | –CH$_2$–C$_6$H$_5$ | CH$_3$ | 60 | 122–123 | ethyl acetate - hexane |

TABLE 11

[Structure: similar bicyclic compound with R³, R, CONR¹R² groups]

| Example No. | R³ | R | R¹ | R² | Yield (%) | Melting Point (°C.) | Solvent for Recrystallization |
|---|---|---|---|---|---|---|---|
| 61 | 7,8-OCH$_2$O— | H | –C$_6$H$_4$–Cl | H | 80 | 237–238 | ethyl acetate |
| 62 | 7,8-OCH$_2$O— | H | –CH$_2$–C$_6$H$_5$ | CH$_3$ | 42 | 104–105 | ethyl acetate - hexane |
| 63 | 8-CH$_3$S | H | –C$_6$H$_4$–CH$_2$PO(OC$_2$H$_5$)$_2$ | H | 90 | 216–217 | ethanol - chloroform |

TABLE 11-continued

| Example No. | R³ | R | R¹ | R² | Yield (%) | Melting Point (°C.) | Solvent for Recrystallization |
|---|---|---|---|---|---|---|---|
| 64 | 8-CH₃S | H | —⟨C₆H₄⟩—PO(OC₂H₅)₂ | H | 68 | 237–238 | ethanol |
| 65 | 8-CH₃S | H | —⟨C₆H₄⟩—CH₂PO(OC₂H₅)₂ | H | 60 | 157–158 | ethanol |
| 66 | 8-CH₃S | H | —⟨C₆H₄⟩—Cl | H | 57 | 249–250 | ethyl acetate |
| 67 | H | H | —⟨C₆H₄⟩—Cl | H | 84 | 204–205 | methanol - dichloromethane |
| 68 | H | H | —⟨C₆H₄⟩—CH₂PO(OC₂H₅)₂ | H | 78 | 221–222 | ethanol - chloroform |

TABLE 12

| Example No. | R³ | R | R¹ | R² | Yield (%) | Melting Point (°C.) | Solvent for Recrystallization |
|---|---|---|---|---|---|---|---|
| 76 | 7,8-OCH₂CH₂O— | H | —⟨C₆H₄⟩—Cl | H | 93 | 279–280 | methanol - chloroform |
| 77 | 7,8-OCH₂CH₂O— | H | —⟨C₆H₄⟩—PO(OC₂H₅)₂ | H | 60 | 234–235 | ethanol |
| 78 | 7,8-OCH₂CH₂O— | H | —⟨C₆H₄⟩—CH₂PO(OC₂H₅)₂ | H | 93 | 245–246 | ethanol - chloroform |

TABLE 12-continued

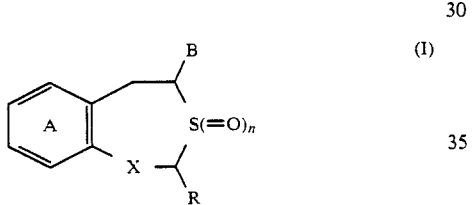

| Example No. | R³ | R | R¹ | R² | Yield (%) | Melting Point (°C.) | Solvent for Recrystallization |
|---|---|---|---|---|---|---|---|
| 79 | 9-(CH₃)₂CH | H | —⟨phenyl⟩Cl | H | 80 | 186–187 | ethyl acetate - hexane |
| 80 | 9-(CH₃)₂CH | H | —⟨phenyl⟩PO(OC₂H₅)₂ | H | 76 | 206–207 | ethyl acetate |
| 81 | 9-(CH₃)₂CH | H | —⟨phenyl⟩CH₂PO(OC₂H₅)₂ | H | 85 | 215–216 | ethyl acetate |

What we claim is:

1. A sulfur-containing heterocyclic compound of the formula (I):

$$\text{(I)}$$

wherein ring A is a benzene ring which may be substituted by 1 to 4 substituents, which are the same or different, selected from the group consisting of:
(1) halogen;
(2) nitro,
(3) C$_{1-10}$ straight-chain or branched alkyl or C$_{3-7}$ cycloalkyl group which may be substituted by 1 to 3 substituents, which are the same or different, selected from the group consisting of a halogen, hydroxyl, C$_{1-6}$ alkoxy, mono- or di(C$_{1-6}$ alkoxy)-phosphoryl and phosphono group,
(4) (i) hydroxyl, or
(ii) C$_{1-10}$ straight-chain or branched alkoxy, C$_{4-6}$ cycloalkoxy, C$_{2-10}$ alkenyloxy, C$_{6-19}$ aralkyloxy, C$_{2-10}$ alkanoxyloxy or C$_{6-14}$ aryloxy group which may be substituted by 1 to 3 substituents, which are the same or different, selected from the group consisting of a halogen, hydroxyl, C$_{1-6}$ alkoxy and mono- or di(C$_{1-6}$ alkoxy)phosphoryl group,
(5) (i) mercapto, or
(ii) C$_{1-10}$ straight-chain or branched alkylthio, C$_{4-6}$ cycloalkylthio, C$_{7-19}$ aralkylthio or C$_{2-10}$ alkanoylthio group which may be substituted by 1 to 3 substituents, which are the same or different, selected from the group consisting of a halogen, hydroxyl, C$_{1-6}$ alkoxy and mono- or di(C$_{1-6}$ alkoxy)phosphoryl group,
(6) amino group which may be substituted by 1 or 2 substituents, which are the same or different, selected from a group consisting of a C$_{1-10}$ alkyl, C$_{2-10}$ alkenyl, C$_{6-14}$ aryl and C$_{7-19}$ aralkyl group wherein the substituent may be further substituted by a halogen, C$_{1-3}$ alkoxy, mono- or di(C$_{1-6}$ alkoxy)phosphoryl or phosphono group,
(7) C$_{1-19}$ acyl group,
(8) mono- or dialkoxyphosphoryl,
(9) phosphono,
(10) aryl group which may be substituted by 1 to 3 substituents, which are the same or different, selected from the group consisting of a C$_{1-6}$ alkyl, halogen, hydroxyl and C$_{1-6}$ alkoxy group,
(11) C$_{7-19}$ aralkyl group which may be substituted by 1 to 3 substituents, which are the same or different, selected from the group consisting of a C$_{1-6}$ alkyl, halogen, hydroxyl and C$_{1-6}$ alkoxy group and
(12) 5- or 6-membered aromatic heterocyclic group having 1 to 4 nitrogen, oxygen and/or sulfur atoms, which may be substituted by 1 to 3 substituents, which are the same or different, selected from the group consisting of a C$_{1-6}$ alkyl, halogen, hydroxyl and C$_{1-6}$ alkoxy group;

R is (i) a hydrogen atom or (ii) a C$_{1-10}$ alkyl, C$_{2-10}$ alkenyl, C$_{6-14}$ aryl or C$_{7-19}$ aralkyl group which may be substituted by a 5- or 6-membered aromatic heterocyclic group having 1 to 4 nitrogen, oxygen and/or sulfur atoms, halogen, dialkoxyphosphoryl or phosphono group;

B is a carboxyl group which may be esterified or amidated, X is —CH(OH)— or —CO—, and n is an integer of 0, 1 or 2, or its salt.

2. A compound of claim 1, wherein the ring A is a benzene ring substituted by 1 to 4 substituents, which are the same or different, selected from the group consisting of:
(1) halogen,
(2) C$_{1-10}$ straight-chain or branched alkyl or C$_{3-7}$ cycloalkyl group which may be substituted by 1 to 3 substituents, which are the same or different, selected from the group consisting of a halogen, hydroxyl, $C_{1-6}$ alkoxy, mono- or di($C_{1-6}$ alkoxy)-phosphoryl and phosphono group,
(3) (i) hydroxyl, or
(ii) $C_{1-10}$ straight-chain or branched alkoxy, $C_{4-6}$ cycloalkoxy, $C_{2-10}$ alkenyloxy, $C_{6-19}$ aralkyloxy, $C_{2-10}$ alkanoyloxy or $C_{6-14}$ aryloxy group which may be substituted by 1 to 3 substituents, which are the same or different, selected from the group consisting of a halogen, hydroxyl, $C_{1-6}$ alkoxy and mono- or di($C_{1-6}$ alkoxy)phosphoryl group,
(4) (i) mercapto, or
(ii) $C_{1-10}$ straight-chain or branched alkylthio, $C_{4-6}$ cycloalkylthio, $C_{7-19}$ aralkylthio or $C_{2-10}$ alkanoylthio group which may be substituted by 1 to 3 substituents, which are the same or different, selected from the group consisting of a halogen, hydroxyl, $C_{1-6}$ alkoxy and mono- or di($C_{1-6}$ alkoxy)phosphoryl group,
(5) amino group which may be substituted by 1 or 2 substituents, which are the same or different, selected from the group consisting of a $C_{1-10}$ alkyl, $C_{2-10}$ alkenyl, $C_{6-14}$ aryl and $C_{7-19}$ aralkyl group wherein the substituent may be further substituted by a halogen, $C_{1-3}$ alkoxy, mono- or di($C_{1-6}$ alkoxy)phosphoryl or phosphono group, or its salt.

3. The compound of claim 1, wherein B is an amidated carboxyl group of the formula —CON($R^1$)($R^2$) in which $R^1$ and $R^2$ are independently selected from the group consisting of (a) hydrogen, (b) a hydrocarbon group selected from the group consisting of $C_{1-10}$ alkyl, $C_{2-10}$ alkenyl, $C_{6-14}$ aryl and $C_{7-19}$ aralkyl and (c) a heterocyclic group selected from the group consisting of 5- to 7-membered heterocyclic groups containing 1 sulfur, nitrogen or oxygen atom, a 5- or 6-membered heterocyclic group containing 2 to 4 nitrogen atoms and a 5- or 6-membered heterocyclic group containing 1 to 2 nitrogen atoms and one sulfur or oxygen atom, any of which can be optionally condensed with a 6-membered ring containing 2 or fewer nitrogen atoms, a benzene ring or a 5-membered ring containing one sulfur atom, the hydrocarbon and heterocyclic groups being optionally substituted with up to three members, which may be the same or different, selected from the group consisting of halogen, hydroxy, $C_{1-6}$ alkoxy, amino which may be substituted with $C_{1-6}$ alkyl or $C_{1-10}$ acyl, carbamoyl which may be substituted with $C_{1-6}$ alkyl, $C_{1-6}$ alkoxy carbonyl, mono- or di-alkoxyphosphoryl, phosphono or a 5- or 6-membered aromatic heterocyclic group having 1 to 4 nitrogen, oxygen and/or sulfur atoms, which may be substituted by 1 to 3 substituents, which are the same or different, selected from the group consisting of halogen, $C_{1-6}$ alkyl, hydroxyl and $C_{1-6}$ alkoxy, or its salt.

4. A compound of claim 1 wherein the ring A is a benzene ring substituted by one or two substituents of a straight or branched cain alkyl having 1 to 10 carbon atoms, an alkoxy having 1 to 10 carbon atoms, an alkylthio having 1 to 10 carbon atoms and/or halogen, or its salt.

5. A compound of claim 1 wherein the ring A is a benzene ring substituted by an alkylenedioxy having 1 to 3 carbon atoms, or its salt.

6. A compound of claim 1 wherein the ring A is a benzene ring substituted by methyl, methoxy or methylthio, or its salt.

7. A compound of claim 1 wherein the ring A is a benzene ring substituted by a chlorine, or its salt.

8. A compound of claim 1 wherein R is hydrogen atom, an alkyl group having 1 to 6 carbon atoms or a phenyl group, or its salt.

9. A compound of claim 1 wherein B is carboxyl or $C_{1-10}$ alkoxycarbonyl group, or its salt.

10. A compound of claim 3 wherein $R^1$ is hydrogen atom or an alkyl group having 1 to 10 carbon atom, and $R^2$ is a phenyl or phenyl-$C_{1-3}$ alkyl group which may be substituted by a halogen, a $C_{1-6}$ alkoxy, a mono- or di-alkoxyphosphoryl, a mono- or di-alkoxyphosphoryl-$C_{1-3}$ alkyl or a $C_{1-6}$ alkoxycarbonyl or a 5- or 6-membered heterocyclic group having one or two nitrogen atoms, or one nitrogen atom and one sulfur atom which may be substituted by a phenyl, or its salt.

11. A compound of claim 1 wherein X is —CO—, and n is 0, or its salt.

12. A compound of claim 1 which is N-(diethoxyphosphorylmethylphenyl)-7,8-dimethoxy-5-oxo-1,2,4,5-tetrahydro-3-benzothiepine-2-carboxamide, N-(4-diethoxyphosphorylphenyl)-7-methyl-5-oxo-1,2,4,5-tetrahydro-3-benzothiepine-2-carboxamide, N-benzyl-N-methyl-7-methyl-5-oxo-1,2,4,5-tetrahydro-3-benzothiepine-2-carboxamide or trans-N-(4-chlorophenyl)-4,7,8-trimethyl-5-oxo-1,2,4,5-tetrahydro-3-benzothiepine-2-carboxamide.

13. A prophylactic or therapeutic composition for osteoporosis which comprises a bone resorption inhibitory amount of a compound of the formula (I) as claimed in claim 1 or its pharmaceutically salt and a pharmaceutically acceptable carrier or excipient.

14. A composition of claim 13 wherein the compound of the formula (I) is one as claimed in any one of claims 4, 9, 10–12, 2 or 3.

15. A method for preventing or treating osteoporosis comprising administering an effective amount of a compound of the formula (I) of claim 1 or its pharmaceutically acceptable salt optionally together with a pharmaceutically acceptable carrier or excipient to a patient suffering from osteoporosis.

* * * * *